United States Patent [19]

Hiyama

[11] Patent Number: 5,187,579
[45] Date of Patent: Feb. 16, 1993

[54] MEDICAL IMAGE DISPLAYING METHOD AND APPARATUS

[75] Inventor: Keiichi Hiyama, Akishima, Japan

[73] Assignee: Olympus Optical Co., Ltd., Tokyo, Japan

[21] Appl. No.: 643,248

[22] Filed: Jan. 18, 1991

[30] Foreign Application Priority Data

Jan. 19, 1990 [JP] Japan .................... 2-10228

[51] Int. Cl.⁵ .................... H04N 7/18; H04N 5/262
[52] U.S. Cl. .................... 358/183; 358/98
[58] Field of Search .................... 358/93, 98, 183

[56] References Cited

U.S. PATENT DOCUMENTS

| | | | |
|---|---|---|---|
| 4,727,417 | 2/1988 | Kanno et al. | 358/98 |
| 4,768,089 | 8/1988 | Kato | 358/98 |
| 4,841,363 | 6/1989 | Ams et al. | 358/98 |
| 5,029,016 | 7/1991 | Hujama et al. | 358/98 |
| 5,031,036 | 7/1991 | Kikuchi | 358/98 |

*Primary Examiner*—John K. Peng
*Attorney, Agent, or Firm*—Armstrong, Westerman, Hattori, McLeland & Naughton

[57] ABSTRACT

A medical image displaying method wherein, while retaining the characteristics of the images of first observed image data, other image data are synthesized with the first observed image data to produce second image data having a plurality of observed image data including the first observed image data and these second image data are displayed in a TV monitor so that a plurality of observed images may be simultaneously displayed without being influenced by the color reproductivity of the TV monitor and without deteriorating the characteristics of the observed images.

15 Claims, 16 Drawing Sheets

FIG.19

| APPARATUS | APPARATUS CODE | HORIZONTAL (LATERAL) RANGE | VERTICAL (LONGITUDINAL) RANGE | STANDARD | COLOR | OTHERS |
|---|---|---|---|---|---|---|
| VIDEO PROCESSOR A | VA | 301~600 | 101~400 | NTSC | RGB | |
| VIDEO PROCESSOR B | VB | 251~550 | 121~380 | HDTV | RGB | |
| VIDEO PROCESSOR C | VC | 201~500 | 101~400 | NTSC | RGB | CIRCULAR |
| ULTRASONIC APPARATUS A | UA | 0~640 | 0~492 | NTSC | B/W | |
| | | | | | | |

FIG.20

| RECORDED IMFORMATION DATA | CONTRACTED IMAGE DATA | OVSERVED IMAGE DATA |
|---|---|---|

MEDICAL IMAGE DISPLAYING METHOD AND APPARATUS

BACKGROUND OF THE INVENTION

1. Field of the Invention

This invention relate to a medical image displaying method and apparatus whereby an accurate diagnosis can be made.

2. Related Art Statement

Recently there is extensively used an endoscope apparatus whereby an organ or the like within a body cavity can be observed, examined or diagnosed with a monitor picture by inserting an elongate insertable part into the body cavity and using such imaging means as a solid state imaging device.

There is also extensively used an ultrasonic diagnosing apparatus whereby the state of the organ within the body cavity can be observed, examined or diagnosed with a monitor picture by irradiating the organ within the body cavity with ultrasonic waves and using the reflection or transmissivity of the ultrasonic waves.

There is also used or suggested another diagnosing apparatus other than the above described diagnosing apparatus whereby the state of a living body can be observed, examined or diagnosed by using an electronic (electric) means.

An image filing apparatus recording the state of the above mentioned organ within the body cavity in such recording medium as for example, a photomagnetic disc can be connected to the above described diagnosing apparatus.

In the above mentioned image filing apparatus, the above mentioned observed image is recorded in the above mentioned recording medium as observed image data of a predetermined number of bits in which the observed image is divided, for example, by 640 dots horizontally and 480 dots vertically and the respective R, G and B color signal levels are quantized so as to be, for example, 8 bits. Further, in the above mentioned observed image data, the number of bits may be contracted as by a compressing means so that many of the above mentioned observed image data may be recorded in one single body of the above mentioned recording medium.

As a precise diagnosis can be made with a time after the observation, the above mentioned image filing apparatus will be extensively used in the future.

Now, when a plurality of observed images reproduced from the above mentioned image filing apparatus are to be simultaneously displayed, compared and diagnosed, conventionally the observed images have been displayed one by ore in respective TV monitors by using a plurality of TV monitors, or a plurality of images have been simultaneously displayed in one TV monitor.

However, in case the observed images are displayed one by one in a plurality of TV monitors, they will be able to be displayed without decreasing the number of displayed dots of the observed image but, on the other hand, it will be difficult to prepare and arrange a plurality of TV monitors having the same color productivity, even if the same observed image is displayed in a plurality of TV monitors, it will have a different color reproductivity, therefore, even if the observed images to be compared are displayed one by one in a plurality of TV monitors, there will be no assurance that the color reproductivities of the respective TV monitors will be the same and therefore it will be difficult to make an accurate comparison and diagnosis.

On the other hand, in case a plurality of observed images to be compared and diagnosed are to be simultaneously displayed, there will be no problem regarding the color reproductivity but, in simultaneously displaying a plurality of observed images in one TV monitor, it will be difficult to contract the respective observed images so as to be housed within the TV monitor and to decrease the number of the displayed dots and therefore there will be problems in that the observed images will be much reduced in resolution and, as a result, the respective images will be difficult to compare and diagnose.

OBJECTS AND SUMMARY OF THE INVENTION

An object of this invention is to provide a medical image displaying method and apparatus whereby, when a plurality of observed images are to be simultaneously displayed, compared and diagnosed, the color reproductivity will not be influenced by the TV monitor, that is to say, the color reproductivities of the respective observed images to be simultaneously displayed will be made the same, a plurality of images will be able to be simultaneously displayed without decreasing the number of displayed dots of the above mentioned respective observed images, the resolution of the observed images will not be reduced and the observed images will be able to be accurately compared and diagnosed.

Another object cf this invention is to provide a medical image displaying method and apparatus whereby a plurality of observed images can be simultaneously displayed without decreasing the number of dots displayed in one TV monitor.

A further object of this invention is to provide a medical image displaying method and apparatus wherein one of a plurality of observed images to be displayed simultaneously is an observed image (color) of a video scope and two of them are black and white observed images of an ultrasonic scope.

The medical image displaying method of this invention is to simultaneously display a plurality of observed images and is a method whereby second image data are produced by synthesizing other image data with first observed image data while retaining the characteristics of the first observed image data and are displayed in a TV monitor.

Also, the medical image displaying apparatus of this invention is able to simultaneously display a plurality of observed images and is provided with an image synthesizing means for producing second image data by synthesizing other image data with first observed image data while retaining the characteristics of the first observed image data.

The other features and advantages of this invention will become apparent enough with the following explanation.

BRIEF DESCRIPTION OF THE DRAWINGS

FIG. 1 is a formation diagram showing the formation of a medical image displaying apparatus.

FIG. 2 is a flow chart relating to the process of observed image data.

FIG. 3 is a flow chart relating to a main image displaying process of displaying images.

FIGS. 4 to 6 are flow charts relating to auxiliary image displaying processes.

FIG. 7 is a flow chart relating to a data inputting process on images.

FIG. 8 is an explanatory view showing a recording type to a recording medium.

FIGS. 9 and 10 are explanatory views of pictures displayed by a main image displaying process.

FIGS. 11 to 13 are explanatory views of pictures displayed by an auxiliary image dislplaining process.

FIG. 14 is a formation diagram showing the formation of a medical image displaying apparatus.

FIG. 15 is a formation explaining diagram showing an ultrasonic diagnosing apparatus.

FIG. 16 is a flow chart relating to an image reproducing process.

FIG. 17 is an explanatory diagram showing images to a monitor.

FIGS. 18 to 23 relate to the third embodiment of the present invention.

FIG. 18 is a formation diagram showing the formation of a medical image displaying apparatus.

FIG. 19 is an explanatory view of a control table of the apparatus.

FIG. 20 is an explanatory view showing a recording type to a recording medium.

FIG. 21 is an explanatory view showing a display of a diagnosing apparatus.

FIG. 22 is a flow chart relating to the reproduction of an image.

FIG. 23 is an explanatory view of pictures displayed by an image displaying process.

DETAILED DESCRIPTION OF THE PREFERRED EMBODIMENTS

The medical image displaying apparatus of the first embodiment explained with reference to FIGS. 1 to 13 is largely divided into an observing system and diagnosing system.

Figure 1:
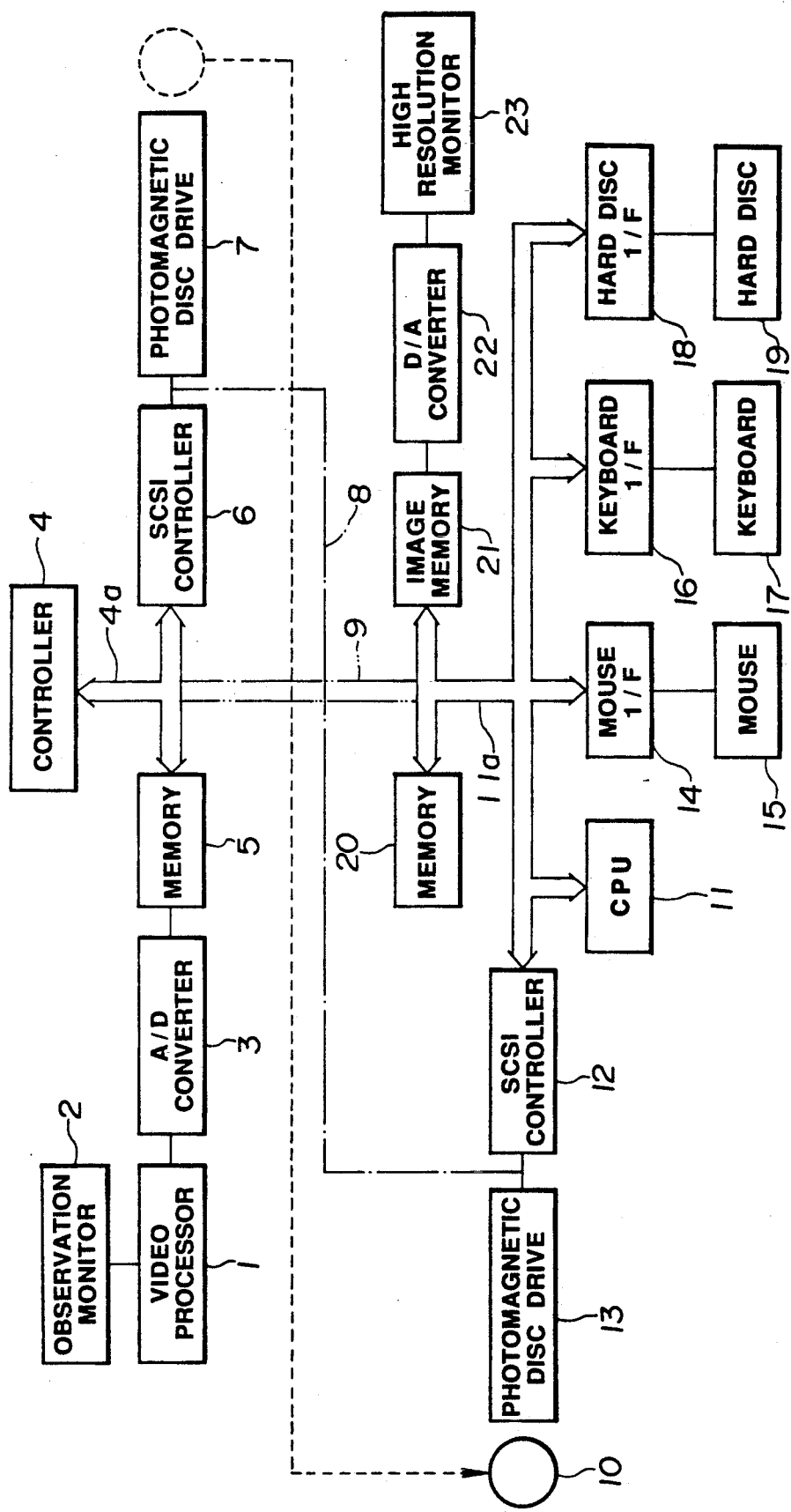
FIGS. 1 to 13 relate to the first embodiment of the present invention.

As shown in FIG. 1, the above mentioned observing system comprises video processor 1 connected, for example, with an electronic endoscope not illustrated, obtaining an imaging signal from this electronic endoscope and converting it to a video signal, an observation monitor 2 displaying the video signal from this video processor 1, an A/D converter 3 converting the analog R, G and B video signals of the above mentioned video processor to observed image data which are digital signals, a controller 4 controlling the later described memory 5 and SCSI controller 6, a memory 5 memorizing by the control of the above mentioned controller 4 the above described observed image data by the above mentioned A/D converter 3, the SCSI (small computer system interface) controller 6 delivering by the control of the above mentioned controller 4 the observed image data memorized in the above mentioned memory 5 to the later described photomagnetic disc drive 7 and the photomagnetic disc drive 7 recording the observed image data of the above mentioned memory 5 input from this SCSI controller 6 into, for example, a photomagnetic disc 10 which is a large capacity recording medium.

The above mentioned video processor 1 is connected at the video signal output end to the above mentioned observation monitor 2 and at the R,G,B video signal output end to the above mentioned A/D converter 3 at the input end.

The above mentioned A/D converter 3 is connected at the output end to the above mentioned memory 5 at the data signal end.

The above mentioned controller 4 is connected at the control signal end and data signal end through a bus line 4a to the above mentioned memory 5 and SCSI controller 6 at the control signal end and data signal end.

The above mentioned SCSI controller 6 is connected at the SCSI line end to the above mentioned photomagnetic disc drive 7. This SCSI line can control a plurality of microprocessor peripheral apparatus and transmit and receive data by using parallel lines (parallel core line group).

For example, a photomagnetic disc 10 which is a large capacity recording medium is to be inserted into the above mentioned photomagnetic disc drive 7.

The observed image, for example, by an electronic endoscope converted to a video signal by the above mentioned video processor 1 is to be displayed as an observed image in the above mentioned observation monitor 2. In case it is judged by the operator of the above mentioned video processor 1 to be necessary to record the above described observed image, the above described video signal will be output as analog R,G,B video signals to the above mentioned A/D converter 3 which will quantize the above mentioned analog R,G,B video signals as predetermined to convert them to digital R,G,B video signals and will output them as observed image data to the above mentioned memory 5.

The above mentioned memory 5 memorizes the observed image data input from the above mentioned A/D converter by the control of the above mentioned controller 4.

The above mentioned controller 4 applies such various data processes as a contracting process to the observed image data memorized in the above mentioned memory 5 and once memorizes the observed image data in the above mentioned memory 5 or outputs them to the SCSI controller 6. In case the observed image data to which various data processes have been applied as described above are once memorized in the memory 5, the above mentioned controller 4 will output the above mentioned observed image data from the above mentioned memory 5 to the above mentioned SCSI controller 6 by a predetermined timing.

The control of the memory 5 and SCSI controller 6 by the above described controller 4 is made by a signal through the above mentioned bus line 4a.

The above mentioned SCSI controller 6 outputs to the above mentioned photomagnetic disc drive 7 the observed image data from the above mentioned memory 5 input as described above and the above mentioned photomagnetic disc drive 7 records the observed image data, for example, in the photomagnetic disc 10.

The above mentioned diagnosing system comprises a microprocessor (called a CPU hereinafter) 11 controlling this diagnosing system, a photomagnetic disc drive 13 reproducing observed image data from the above mentioned photomagnetic disc drive 10 and recording various informations together with these observed image data, an SCSI controller 12 controlling this photomagnetic disc drive 13, a mouse 15 giving an instruction to move a cursor coordinate on a monitor picture to any position, a mouse interface (called a mouse I/F hereinafter) 14 coordinating the signal of this mouse 15 and the signal of the above mentioned CPU 11, a key board 17 inputting various information to be recorded, for example, into the above mentioned photomagnetic disc 10, a key board interface (called a keyboard I/F hereinafter) 16 coordinating the signal of this keyboard 17 and the signal of the above mentioned CPU 11, a hard disc 19 in which are recorded such various data as a practice program and image data cf a menu picture, a hard disc interface (called a hard disc I/F hereinafter) 18 coordinating the signal of this hard disc 19 and the signal of the above mentioned CPU 11, a memory 20 used as various process operating regions of the above mentioned CPU 11, an image memory 21 memorizing displaying digital R,G,B video signals, D/A converter 22 reversely quantizing image data which are digital signals of the above mentioned image memory 21 and converting them to analog R,G,B video signals and a high resolution monitor 23 displaying the analog R,G,B video signals converted by this D/A converter 22.

The control signal end and data signal end of the above mentioned CPU 11 are connected through a bus line 11a to the control signal ends and data signal ends of the above mentioned SCSI controller 12, mouse I/F 14, keyboard I/F 16, hard disc I/F 18, memory 20 and image memory 21.

The SCSI line cf the above mentioned controller 12 is connected to the above mentioned photomagnetic disc drive.

The above mentioned image memory 21 is connected at the data signal end to the above mentioned D/A converter 22 at the input end and this D/A converter 22 is connected at the output end to the above mentioned high resolution monitor 23.

Such large capacity memorizing medium as, for example, the photomagnetic disc 10 is to be inserted into the above mentioned photomagnetic disc drive 13.

The above mentioned CPU 11 is to control through the above mentioned bus line 11a the above mentioned SCSI controller 12, mouse I/F 14, keyboard I/F 16, hard disc I/F 18, memory 20 and image memory 21.

The above mentioned SCSI controller 12 controls the above mentioned photomagnetic disc drive 10, reads out the above described observed image data recorded in the above described observing system, outputs them to the above mentioned memory 20 and records in the above mentioned photomagnetic disc 10 the part codes of the observed image data memorized in the above mentioned memory and the position data in the parts.

The above mentioned memory 20 is to memorize the above described observed image data.

The above mentioned mouse I/F 14 detects a signal corresponding to the physical relative displacement of the above mentioned mouse 15 and outputs the signal to the above mentioned memory 20 which memorizes the above described displacement.

The above mentioned keyboard I/F 16 outputs to the above mentioned memory 20 a signal of character information or the like input from the above mentioned keyboard and the memory 20 memorizes the above described character information or the like.

The above mentioned hard disc I/F 18 reads a program practiced by the above mentioned CFU 11 and image data of a menu picture or the like out of the above mentioned hard disc 19 and outputs them to the above mentioned memory 20 which memorizes the above described program and image data or the like.

The above mentioned CPU 11 operates so as to be displayed as synthesized or singly such image data as observed image data from the above mentioned photomagnetic disc drive, a cursor by the mouse 15, character information by the keyboard 17 and a menu picture from the hard disc 19 memorized as described above in the above mentioned memory 2( by a program memorized in the above mentioned memory 20 is described above.

The image data which are digital signals memorized in the above mentioned image memory 21 as described above are converted to analog R,G,B video signals by the reverse quantization of the above mentioned D/A converter 12 and are output to the above mentioned high resolution monitor 23.

The above mentioned high resolution monitor 23 is to display the analog R,G,B video signals input as described above.

The observed image data recorded in the above mentioned photomagnetic disc 10 are formed of a predetermined number of bits so that, when the above described observed color image is divided, for example, by 640 dots horizontally and 480 dots vertically, the respective R,G,B color signal levels may be quantized to be, for example, 8 bits in response to the respective dots.

The image data of the image displayed in the above mentioned high resolution monitor 23 are formed of a predetermined number of bits so that, when divided, for example, by 1024 dots horizontally and 1280 dots vertically, the respective R,G,B color signal levels may be quantized to be, for example, 8 bits.

The operation of the thus formed medical image displaying apparatus shall be explained.

An observed image, for example, by an electronic endoscope converted to a video signal by the video processor 1 is displayed as an observed image in the observation monitor In case the operator of the above mentioned video processor 1 judges it necessary to record the above described observed image, the above described observed image will be output as analog R,G,B video signals to the above mentioned A/D converter 3, will be converted to digital R,G,B video signals, will be output as observed image data to the memory 5 and will be memorized in this memory 5.

Also, the above mentioned controller 4 applies such various data processes as a contracting process to the observed image data memorized in the above mentioned memory 5 and once memorizes the observed data in the above mentioned memory 5 or outputs them to the SCSI controller 6. In case the observed image data to which various data processes have been applied as described above are once memorized in the memory the above mentioned controller 4 will output the above mentioned observed image data from the above mentioned memory 5 to the above mentioned SCSI controller 6 by a predetermined timing.

The control of the memory 5 and SCSI controller 6 by the above described controller 4 is made by a signal through the above mentioned bus line 4a.

Figure 2:
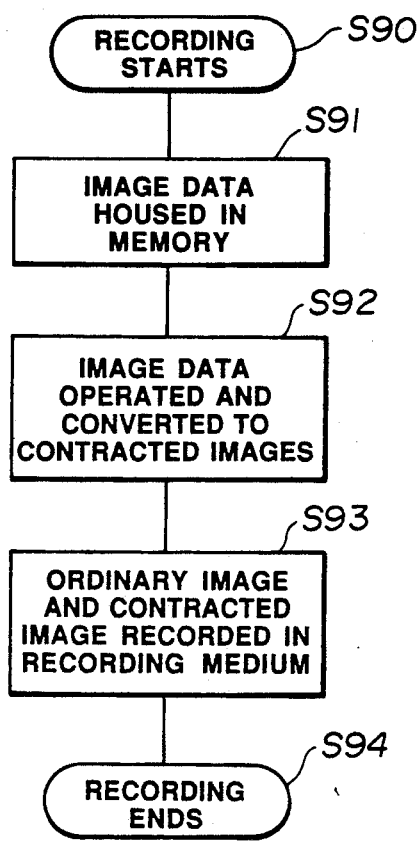

The process of the above described controller 4 shall be explained by using FIG. 2.

In case the operator of the above mentioned video processor 1 judges it necessary to record the above described observed image, the process will be started from Step (called S hereinafter) 90 and, in S91, the above described observed image will be memorized (housed) as observed data in the above mentioned memory 5.

Further, in S92, the above mentioned controller 4 operates to convert to contracted images the observed image data memorized (housed) in the above mentioned memory 5 in S92 and once memorizes (houses) the contracted images or outputs them to the SCSI controller 6.

Further, in S93, the above mentioned controller 4 records in the photomagnetic disc 10 the observed image data which are observed images as described above and the contracted image data of the contracted images of the above mentioned observed images made in the above mentioned S92 through the SCSI controller 6 and photomagnetic disc drive 7 and, in S94, the process ends.

Therefore, in the above mentioned photomagnetic disc 10 are recorded at least the observed image data and the contracted image data made by contracting the above described observed images. In the following explanation, in order to make it easy to distinguish the observed images (observed image data) and contracted images (contracted image data) from each other, the observed images shall be called ordinary observed images.

As shown in FIG. 1, the above mentioned photomagnetic disc 10 is inserted into the photomagnetic drive 13.

The CPU 11 controls through the bus line 11a the SCSI controller 12, mouse I/F 14, keyboard I/F 16, hard disc I/F 18, memory 20 and image memory 21.

In the above mentioned CPU 11, by the above described control, the above mentioned hard disc I/F 18 reads out of the hard disc 19 the programs corresponding to various processes practiced by the CPU 11.

By the above described program, there is practiced the reproducing process of displaying in the high resolution monitor 21 the image data recorded in the above mentioned photomagnetic disc 10.

Figure 3:
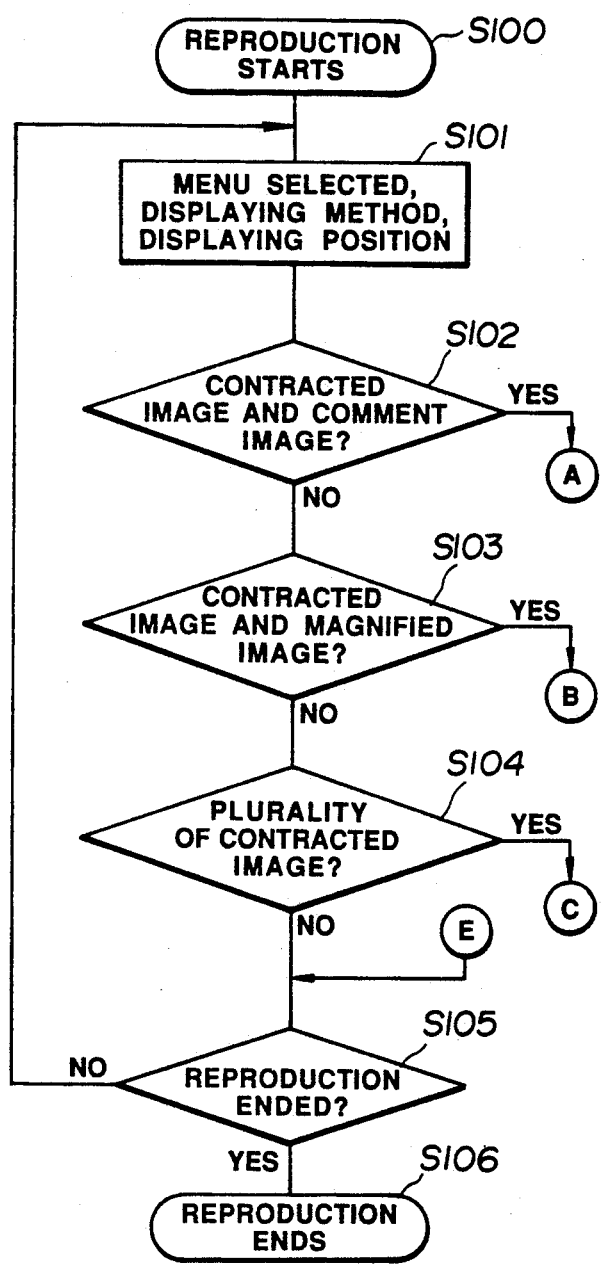
Figure 9:
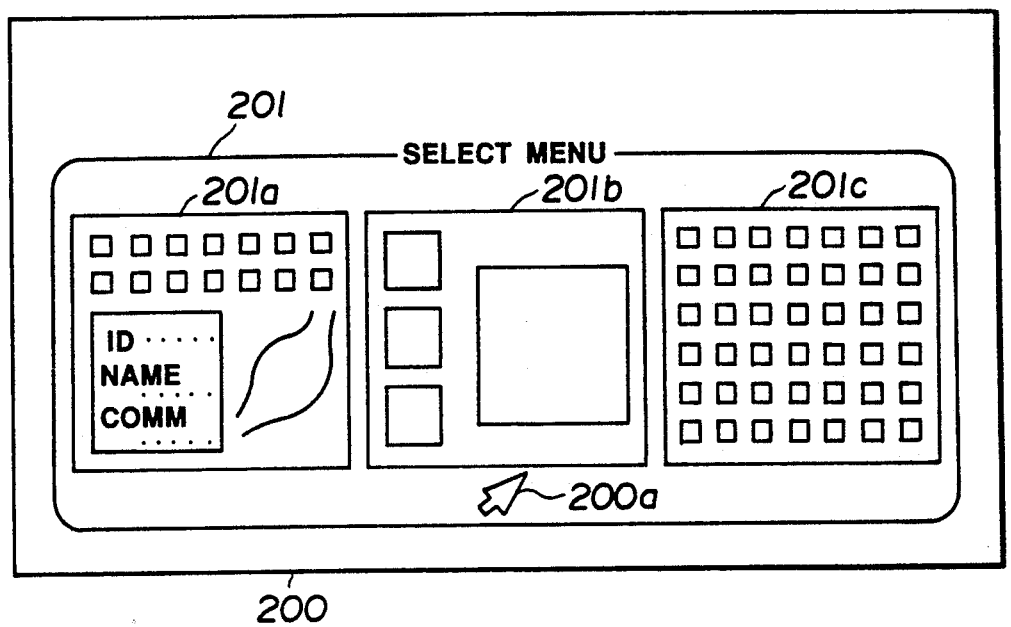
Figure 10:
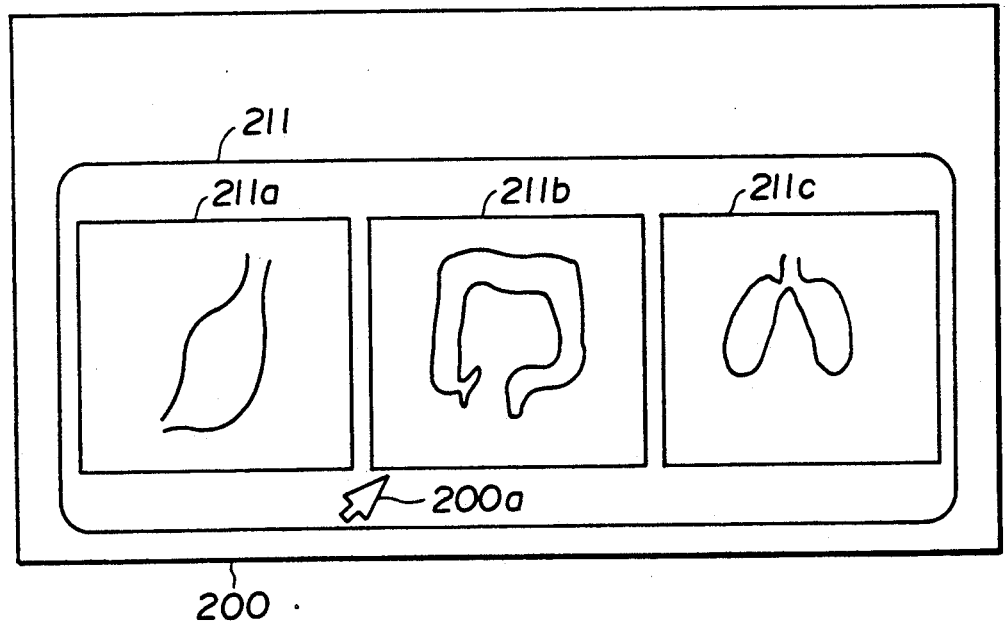

The above described reproducing process shall be explained by using FIGS. 3, 9 and 10.

The reproducing process is started from S100 shown in FIG. 3 and, in S101, a displaying method for selecting the picture formation of the image to be displayed and a displaying method for selecting the part of the image to be displayed are input.

As shown, for example, in FIG. 9, the selected picture of the above described picture formation is by a menu picture 201 displayed on a picture 200 of the above mentioned high resolution monitor 23. This menu picture 201 comprises a designated picture 201a in which is selected a picture formed of a comment image in which are displayed, for example, contracted images and various informations, a designated picture 201b in which is selected a picture formed of a magnified image magnifying and displaying contracted images and observed images and a designated picture 201c in which is selected a picture formed of a plurality of contracted pictures comprising, for example, 42 pictures As shown, for example, in FIG. 10, the above described selected picture of the part to be displayed is by a menu picture 211 displayed on the picture 200 of the above mentioned high resolution monitor 23. This menu picture 211 comprises a designated picture 211a in which is selected, for example, an endoscope observed image, for example, of a stomach, a designated picture 211b in which is selected an endoscope observed image of a large intestine and a designated picture 211c in which is selected an endoscope observed image of a lung.

As shown in FIGS. 9 and 10, a cursor 200a of which the displayed position (coordinate) varies with the moving operation of the above mentioned mouse 15 is also displayed on the above mentioned picture 200.

The picture formation selection and displayed part in the above mentioned S101 are input by moving the above mentioned cursor 200a on a desired designated picture by the operation of the above mentioned mouse 15 and pushing down a switch not illustrated provided, for example, in the mouse 15.

The displaying method input in the above mentioned S101 is judged in S102 to S104. In case it corresponds to the above described displaying method (YES), it will be shifted to the respective processes but, in case it does not correspond (NO), the process will be shifted to S105.

In the above mentioned S105, it is judged whether the reproduction is to end or not. In case the reproduction ends (YES), in S106, the reproducing process will end but, in case the reproduction does not end (NO), the process will be shifted to the process of the above mentioned S101.

Figure 4:
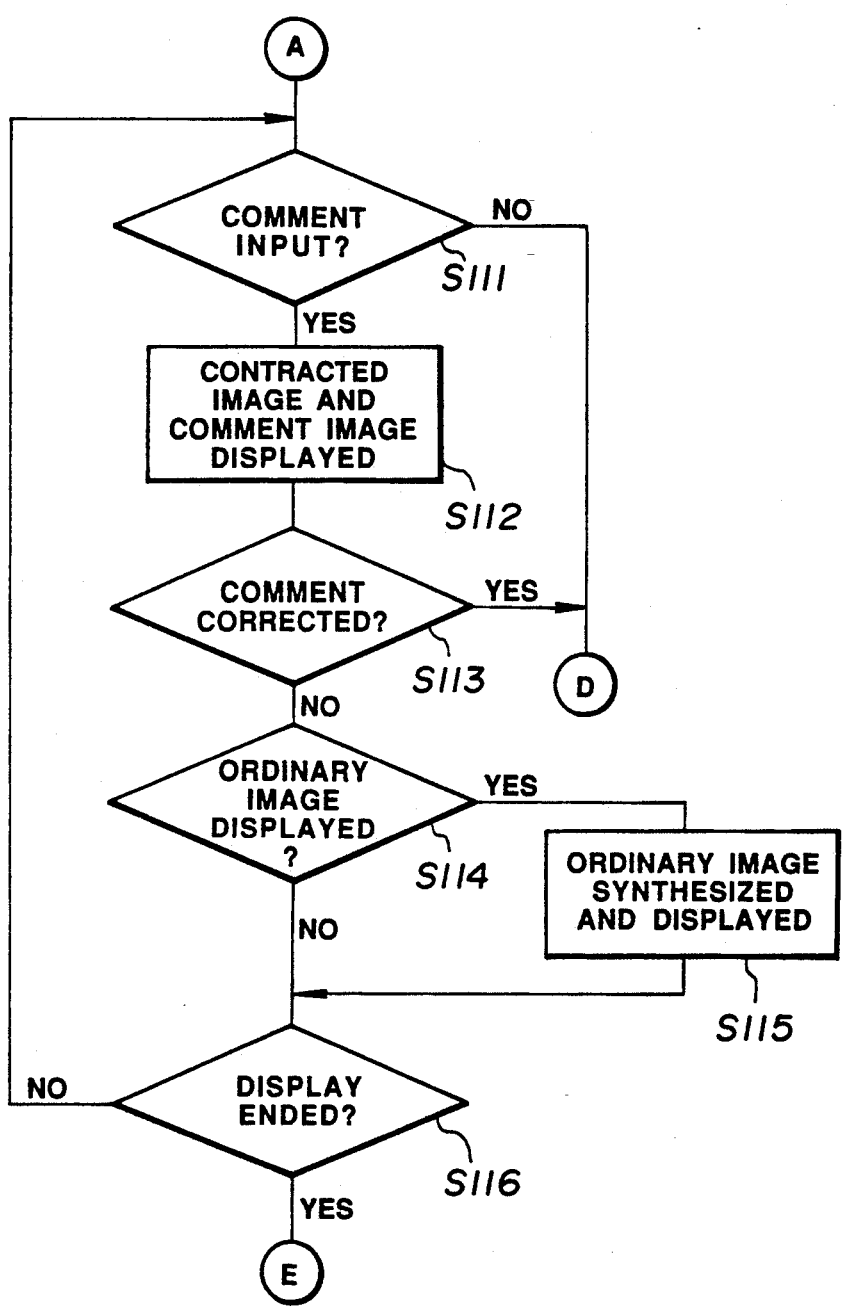
Figure 11:
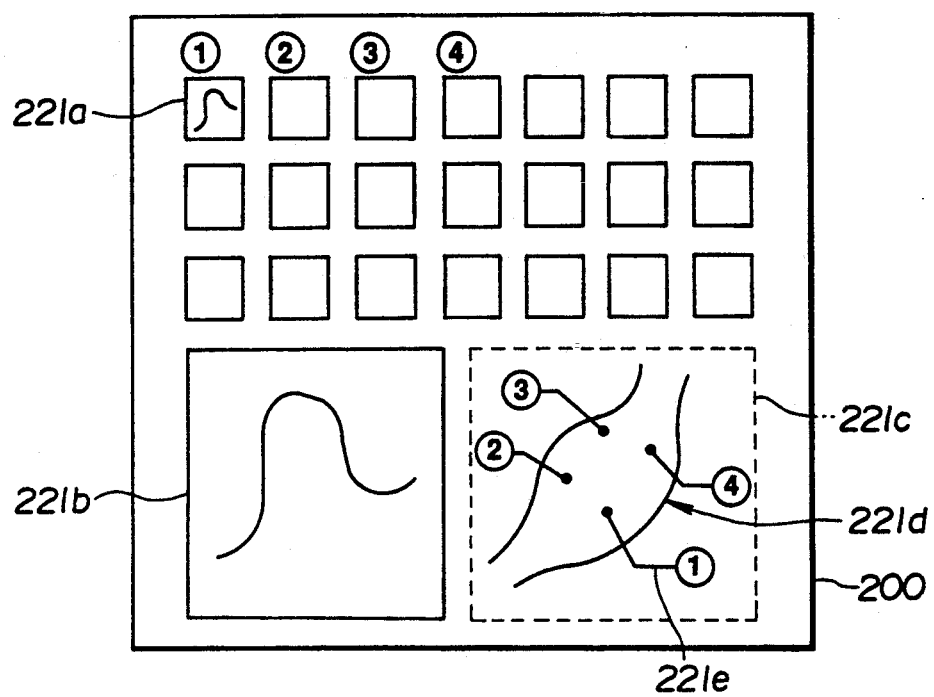

In the above mentioned S102, in case the process of displaying a picture formed of a comment image in which are displayed contracted images and various informations is selected, a process of practicing this process shown, for example, in FIG. 4 will be practiced and the picture shown, for example, in FIG. 11 will be displayed on the picture 200 in the above mentioned high resolution monitor 23.

The above described process of displaying a picture formed of a comment image in which are displayed contracted images and various informations is started from S111 in FIG. 4 and, in the above mentioned S101, it is judged whether such comment as the information relating to the selected displayed part has been already input or not.

In the above mentioned S111, in case the comment has been input (YES), in S112, on the picture 200 of the above mentioned high resolution monitor 23 shown in FIG. 11 will be displayed, for example, 21 contracted images 221a, a comment image 221b which is the information of the examinee not illustrated and a comment image 221c corresponding to the observed image. In the above mentioned comment image 221c are displayed, for example, image data 221d displaying the displayed part and a marker 221e displaying the position (coordinate) of the part of the above mentioned contracted image 221a. The image of such comment as the information of the examinee not illustrated is displayed in the displaying position of the ordinary observed image 221b. Further, reference numerals are attached to the above mentioned markers 221e so as to correspond to the above mentioned contracted images 221a.

In the above mentioned S112, after the picture is displayed, in S113, it is judged whether the above described comment is to be corrected or not. This judgment is input by such generally used inputting method as by the above described mouse 15 or keyboard 17.

In the above mentioned S113, in case it is judged that the comment is not corrected (NO), in S114, it will be judged whether the ordinary observed image corresponding, for example, to the above mentioned contracted image 221a is to be displayed or not. This judgment is input by such generally used inputting method as by the above described mouse 15 or keyboard 17.

In the above mentioned S114, in case it is selected that the ordinary observed image is displayed (YES), in S115, the ordinary image will be synthesized with the image in which are displayed such plurality of contracted images as the contracted images 221a shown in FIG. 11 and which is displayed in the above mentioned S112 and will be displayed. For this ordinary observed image, an image corresponding, for example, to the contracted image 221a is displayed as the ordinary observed image 221b.

In the above mentioned S114, in case it is selected that the ordinary observed image is not displayed (NO) or in the above mentioned S115, after the ordinary observed image is displayed. In S116, it will be judged whether the process of displaying the picture formed of the comment image in which are displayed contracted images and various informations is to end or not. This judgment is input by such generally used inputting method as by the above described mouse 15 or keyboard 17.

In the above mentioned S116, in case the process of displaying the picture formed of the comment image in which are displayed contracted images and various informations is repeated (NO), the process will be shifted to the process from the above mentioned S111 and, in case this process ends (YES), the process will be shifted to the above mentioned S105 shown in FIG. 3.

Figure 7:
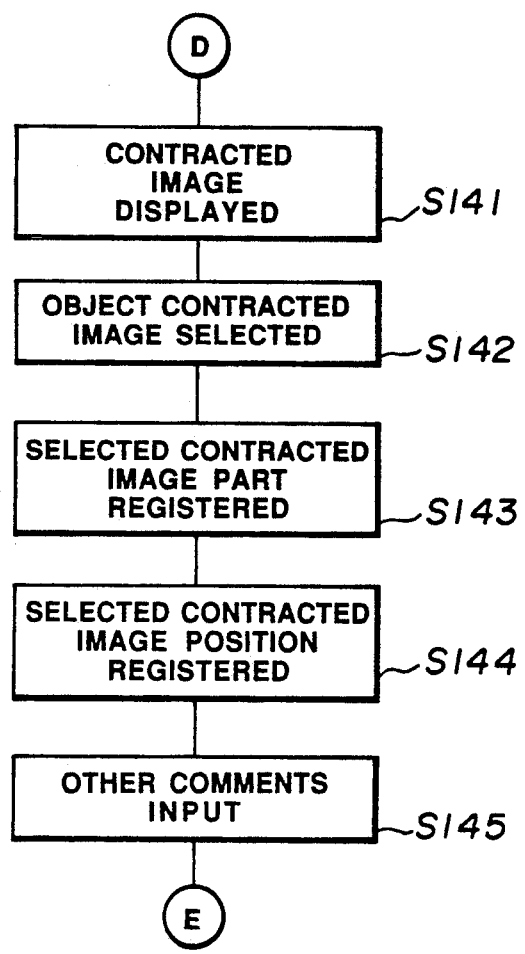

In the above mentioned S111, in case it is judged that the comment is not input and, in the above mentioned S113, in case it is selected to correct the comment, the process will be shifted to the comment inputting process shown, for example, in FIG. 7.

In the above described comment inputting process, in S141, the contracted images are displayed on the picture of the above mentioned high resolution monitor 7, in S142, the contracted image in which the comment is to be input is selected and, by S143, the part of the contracted picture selected as described above is registered. This registration displays the picture shown, for example, in FIG. 10 and is input by such generally used inputting method as by the above described mouse 15 or keyboard 17.

Further, in S144 shown in FIG. 7, the position (coordinate) corresponding to the part of the contracted picture selected as described above is input by an inputting method using the above described mouse 15 for the comment image 221c shown, for example, in FIG. 11.

Further, in S145 shown in FIG. 7, the other comments corresponding to the contracted picture selected as described above are input by such generally used inputting method as, for example, by the above mentioned keyboard 17.

Figure 8:
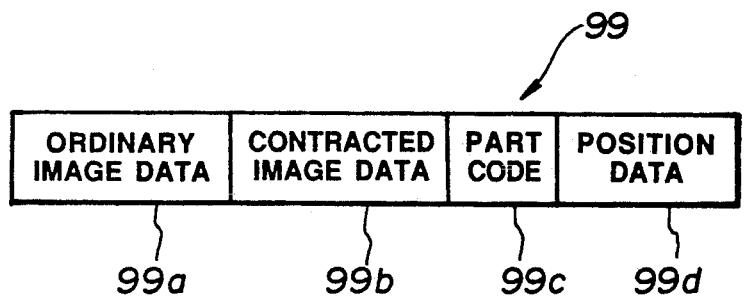

Various data input as described above are recorded as record data, for example, in the above mentioned photomagnetic disc 10 together with the ordinary image data 99a, contracted image data 99b, part code 99c and position (coordinate) data 99d as shown in FIG. 8. The other comments may be recorded together with these record data 99.

By the above mentioned S145 shown in FIG. 7, when the input of the other comments ends, the above described process will be shifted to the above mentioned S105 shown in FIG. 3.

Figure 5:
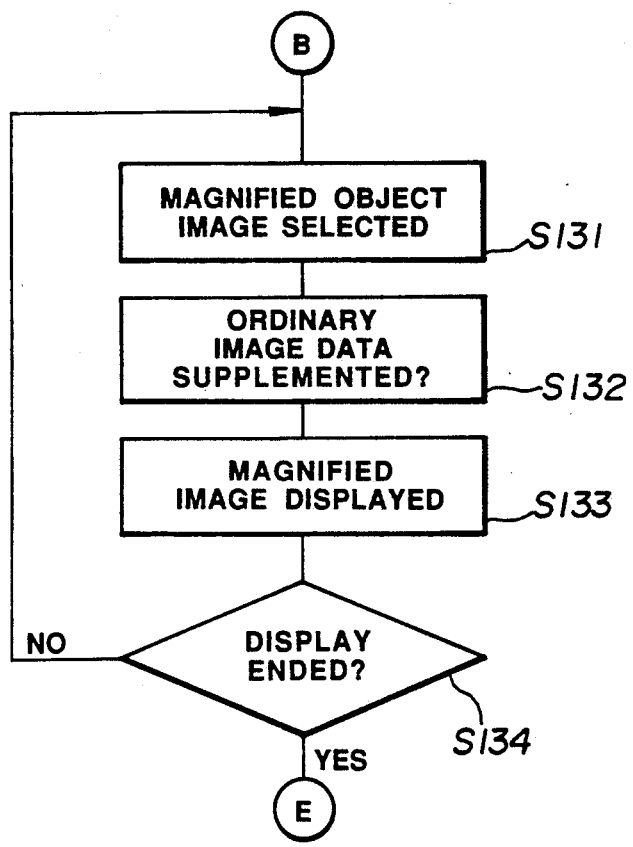
Figure 12:
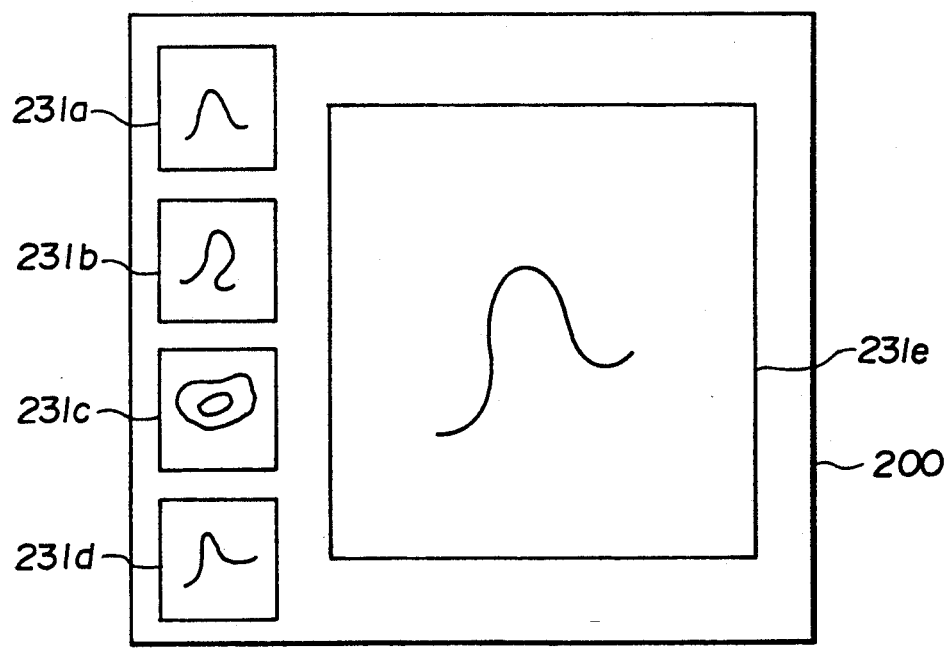

In the above mentioned S103, in case the process of displaying the picture formed of contracted images and a magnified image is selected, the process shown, for example, in FIG. 5 of practicing the above mentioned process will be practiced and the picture shown, for example, in FIG. 12 will be displayed on the picture 200 of the above mentioned high resolution monitor 23.

For example, the contracted pictures 231a to 231d will be displayed in the picture 200 of the above mentioned high resolution monitor 23.

From S131 shown in FIG. 5, the process of displaying the picture formed of contracted images and a magnified image is practiced and, in S131, the observed image to be made a magnified is selected and the process is shifted to S132. In the method of selecting the observed image to be made a magnified picture, the above mentioned contracted pictures 231a to 231d are input by such generally used inputting method as, for example, by the above described mouse 15 or keyboard 17.

In the above mentioned S132, a supplementing process supplementing dots corresponding to the clearance of the standard observed image data on the basis of a predetermined method is applied to the standard observed image data formed of 640×480 dots, for example, as described above so as to be a magnified image formed of 960×720 dots which are, for example, 1.5 times as many and the process is shifted to S133.

In the above mentioned S133, the magnified image to which the supplementing process has been applied is displayed as a magnified image 231e to the picture 200 of the above mentioned high resolution monitor 23 as shown in FIG. 12.

In the above mentioned S133, after the magnified image is displayed, in S134 shown in FIG. 5, it is judged whether the process of displaying the picture formed of contracted images and a magnified image is to be ended or not. This judgment is input by such generally used inputting method as by the above described mouse 15 or keyboard 17.

In the above mentioned S133, in case the process of displaying the picture formed of contracted images and a magnified image is to be repeated (NO), the process will be shifted to the process from the above mentioned S131 and, in case this process is to be ended (YES), the process will be shifted to the above mentioned S105 shown in FIG. 3.

Figure 6:
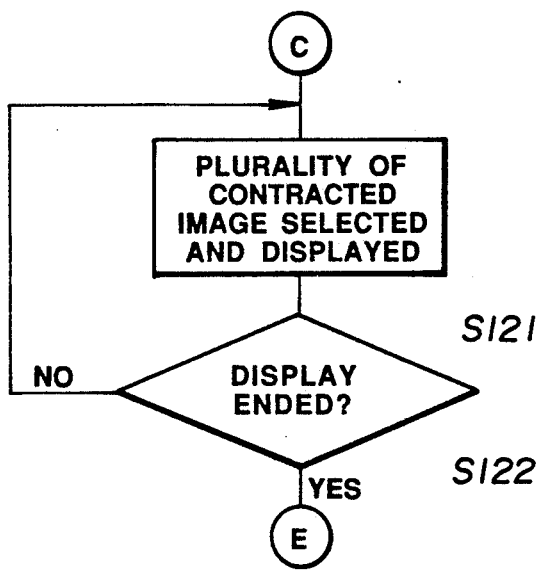
Figure 13:
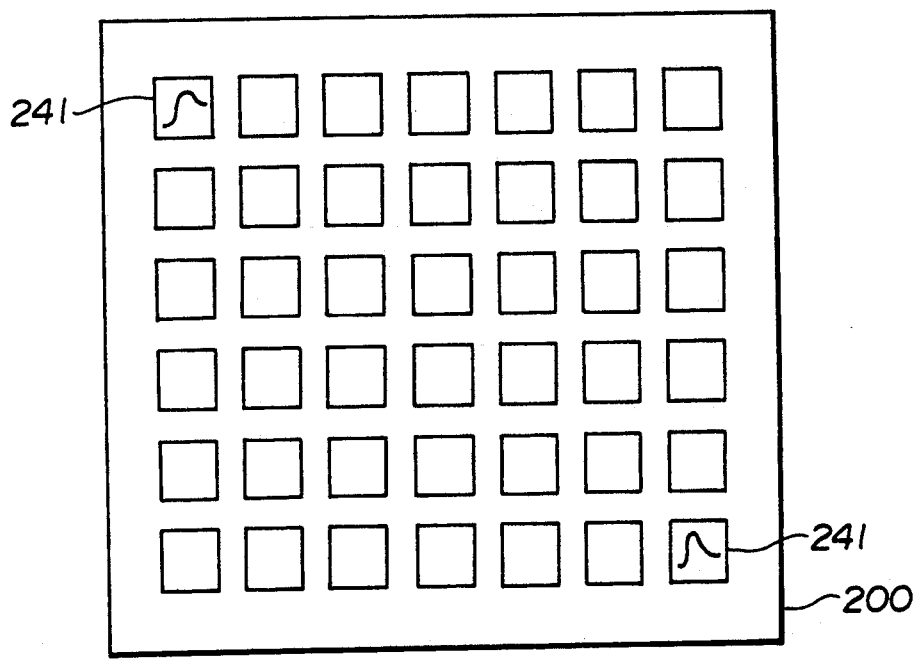

In the above mentioned S104, in case the process of displaying the picture formed of a plurality of contracted images is selected, the process shown, for example, in FIG. 6 of practicing the above mentioned process will be practiced and the picture shown, for example, in FIG. 13 will be displayed on the picture of the above mentioned high resolution monitor 23.

For example, contracted pictures 241 are displayed on the picture 200 of the above mentioned high resolution monitor 23.

From S121 shown in FIG. 6, the process of displaying the picture formed of a plurality contracted images is practiced. In the above mentioned S121, a plurality of contracted image groups are selected and displayed and the process is shifted to S122. The plurality of contracted image groups are selected by such generally used inputting method as, for example, by the above described mouse 15 or keyboard 17.

In the above mentioned S121, after the plurality of contracted images are displayed, in S122, it is judged whether the process of displaying the picture formed of a plurality of contracted images is to be ended or not. This judgment is input by such generally used inputting method as by the above described mouse 15 or keyboard 17.

In the above mentioned S122, in case the process of displaying the picture formed of a plurality of contracted images is repeated (NO), the process will be shifted to the process from the above mentioned S121 and, in case this process is ended (YES), the process will be shifted to the above mentioned S105 shown in FIG. 3.

That is to say in this embodiment, a plurality of observed images and contracted images based on these observed images can be displayed on the same picture, the same diagnosis as the conventionally used diagnosis by photographed observed images can be made, various designations can be input by using a mouse and therefore there is an effect that the operability improves.

By the way, the means of transferring the above described observed image data from the above mentioned observing system to the diagnosing system may be any of such means used in the computer system as a magnetic disc or photomagnetic disc.

Also, the observing means for obtaining observed images is not limited to the endoscope observing apparatus and ultrasonic observing apparatus. Further, the synthesized and displayed image and displaying process are not limited to the above described embodiment.

Also, for example, in case an observing room provided with a video processor 1 or the like and a diagnosing room provided with a high resolution monitor 23 or the like are adjacent to each other or, for example, in case a communicating means can be easily provided by a MODEM (modulator and demodulator) or the like, as shown by the one-point chain line, the above mentioned SCSI controllers 6 and 12 may be connected with each other.

Further, for example, in case such observing system as a video processor 1 and such diagnosing system as a high resolution monitor 23 are provided in the same housing, as shown by the two-point chain line 9 in FIG. 1, the bus line 4a of the above described observing system and the bus line 11a of the above described diagnosing system may be connected with each other.

Thus, according to the above described embodiment of the present invention, a plurality of observed images and information images necessary for the diagnosis can be seen with one high resolution monitor, the diagnosing efficiency is elevated and a precise diagnosis can be made.

The medical image displaying apparatus of the second embodiment explained with reference to FIGS. 14 to 17 is largely divided into an observing system and diagnosing system.

Figure 14:
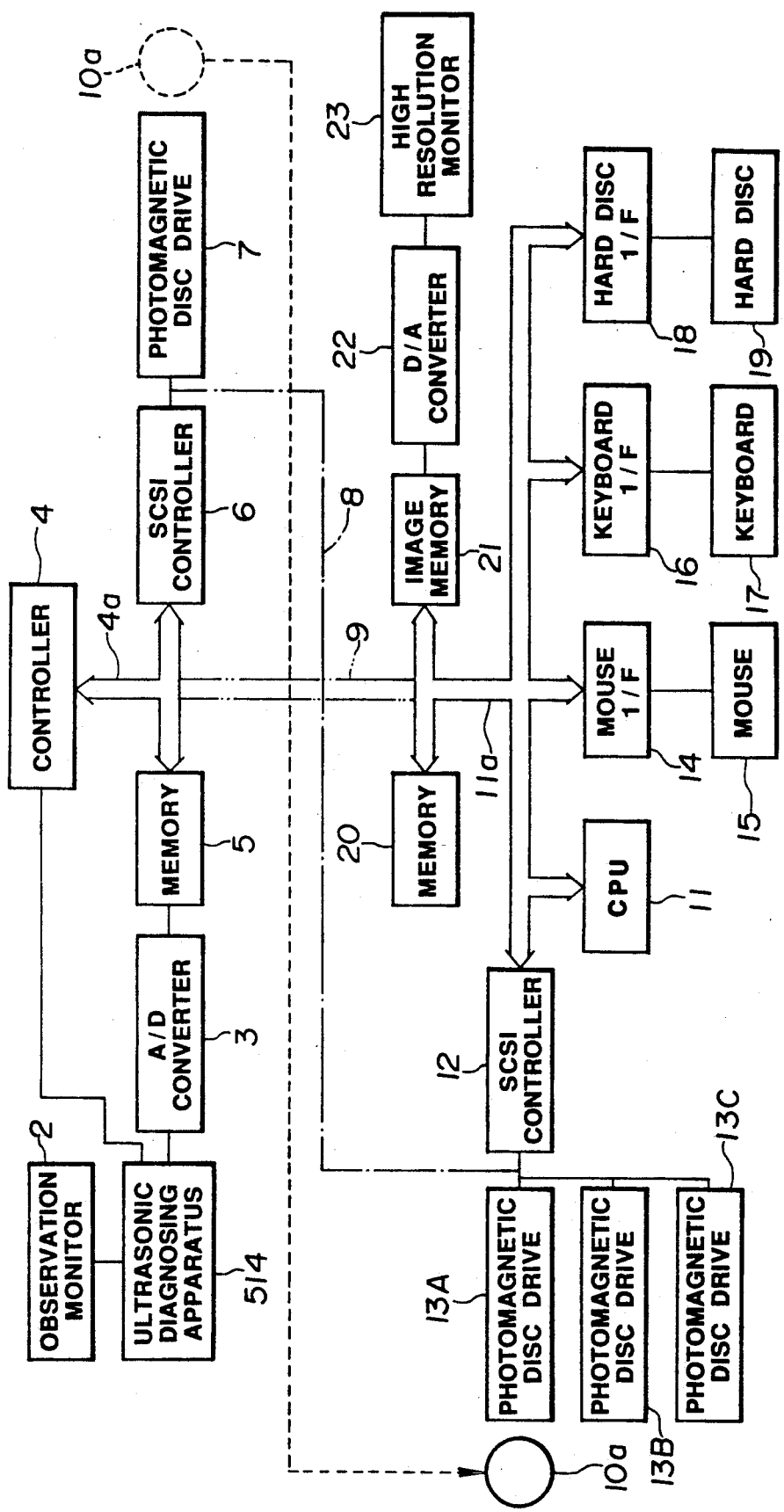
FIGS. 14 to 17 relate to the second embodiment of the present invention.

As shown in FIG. 14, the above mentioned observing system comprises an observation monitor displaying a video image from an ultrasonic diagnosing apparatus 514, an A/D converter converting a black and white video signal of the above mentioned ultrasonic diagnosing apparatus 514 to observed image data which are digital signals, a controller 4 controlling a memory 5 and SCSI controller 6 described later by a control signal or the like from the ultrasonic diagnosing apparatus 514, the memory 5 memorizing by the control of the above mentioned controller 4 the above described observed image data by the above mentioned A/D converter 3, the SISC (small computer system interface) controller 6 delivering the observed image data memorized in the above mentioned memory 5 to a later described photomagnetic disc drive 7 by the control of the above mentioned controller 4 and a photomagnetic disc drive 7 recording, for example, in a photomagnetic disc 10a which is a large capacity memorizing medium the observed image data of the above mentioned memory 5 input from this SCSI controller 6.

The above mentioned ultrasonic diagnosing apparatus 514 is connected at the video signal output end to the above mentioned observation monitor 2 and at the black and white video signal output end to the above mentioned A/D converter 3 at the input end.

The above mentioned A/D converter 3 is connected at the output end to the above mentioned memory 5 at the data signal end.

The above mentioned controller 4 is connected at the control signal end and data signal end to the above mentioned memory 5 and SCSI controller 6 at the control signal end and data signal end by a bus line 4a.

The above mentioned SCSI controller 6 is connected at the SCSI line end to the above mentioned photomagnetic disc drive 7.

For example, a photomagnetic disc 10 which is a large capacity recording medium is to be inserted into the above mentioned photomagnetic disc drive 7.

The observed image, for example, by an ultrasonic endoscope converted to a video signal by the above mentioned ultrasonic diagnosing apparatus 514 is to be displayed as an observed image in the above mentioned observation monitor 2. In case it is judged by the operator of the above mentioned ultrasonic diagnosing apparatus 514 to be necessary to record the above described observed image, the above described video signal will be output as a black and white video signal to the above mentioned A/D converter 3 which will quantize the above mentioned black and white video signal as predetermined to convert it to a digital video signal and will output it as observed image data to the above mentioned memory 5.

The above mentioned memory 5 is to memorize the observed image data input from the above mentioned A/D converter by the control of the above mentioned controller 4.

The above mentioned controller 4 applies such various data processes as a contracting process to the observed image data memorized in the above mentioned memory 5 and once memorizes the observed image data in the above mentioned memory 5 or outputs them to the SCSI controller 6. In case the observed image data to which various data processes have been applied as described above are once memorized in the memory 5, the above mentioned controller 4 will output the above mentioned observed image data from the above mentioned memory 5 to the above mentioned SCSI controller 6 by a predetermined timing.

The control of the memory 5 and SCSI controller 6 by the above described controller 4 is made by a signal through the above mentioned bus line 4a.

The above mentioned SCSI controller 6 outputs to the above mentioned photomagnetic disc drive 7 the observed image data from the above mentioned memory 5 input as described above and the above mentioned photomagnetic disc drive 7 records the observed image data, for example, in the photomagnetic disc 10a.

The above mentioned diagnosing system comprises a microprocessor (called a CPU hereinafter) 11 controlling this diagnosing system, photomagnetic disc drives 13A, B and C reproducing observed image data from the above mentioned photomagnetic disc drive 10a and recording various information together with these observed image data, an SCSI controller 12 controlling these photomagnetic disc drives 13A, B and C, a mouse 15 giving an instruction to move a cursor coordinate on a monitor picture to any position, a mouse interface (called a mouse I/F hereinafter) 14 coordinating the signal of this mouse 15 and the signal of the above mentioned CPU 11, a keyboard 17 inputting various information to be recorded, for example, into the above mentioned photomagnetic disc 10a, a keyboard interface (called a keyboard I/F hereinafter) 16 coordinating the signal of this keyboard 17 and the signal of the above mentioned CPU 11, a hard disc 19 in which are recorded such various data as practice programs and image data of a menu picture, a hard disc interface (called a hard disc I/F hereinafter) 18 coordinating the signal of this hard disc 19 and the signal of the above mentioned CPU 11, a memory 20 used as various process operating regions of the above mentioned CPU 11, an image memory 21 memorizing displaying digital R,G,B video signals, D/A converter 22 reversely quantizing image data which are digital signals of the above mentioned image memory 21 and converting them to analog R,G,B video signals and a high resolution monitor 23 displaying the analog R,G,B video signals converted by this D/A converter 22.

The control signal end and data signal end of the above mentioned CPU 11 are connected through a bus line 11a to the control signal ends and data signal ends of the above mentioned SCSI controller 12, mouse I/F 14, keyboard I/F 16, hard disc I/F 18, memory 20 and image memory 21.

The SCSI line of the above mentioned controller 12 is connected to the above mentioned photomagnetic disc drives 13A, B and C.

The above mentioned image memory 21 is connected at the data signal end to the above mentioned D/A converter 22 at the input end and this D/A converter 22 is connected at the output end to the above mentioned high resolution monitor 23.

Such large capacity memorizing medium as, for example, the photomagnetic disc 10a is to be inserted into the above mentioned photomagnetic disc drive 13.

The above mentioned CPU 11 is to control through the above mentioned bus line 11a the above mentioned SCSI controller 12, mouse I/F 14, keyboard I/F 16, hard disc I/F 18, memory 20 and image memory 21.

The above mentioned SCSI controller 12 controls the above mentioned photomagnetic disc drive 10a, reads out the above described observed image data recorded in the above described observing system, outputs them to the above mentioned memory 20 and records in the above mentioned photomagnetic disc 10a the part codes of the observed image data memorized in the above mentioned memory and the position data in the parts.

The above mentioned memory 20 is to memorize the above described observed image data.

The above mentioned mouse I/F 14 detects a signal corresponding to the physical relative displacement of the above mentioned mouse 15 and outputs the signal to the above mentioned memory 20 which memorizes the above described displacement.

The above mentioned keyboard I/F 16 outputs to the above mentioned memory 20 a signal of character information or the like input from the above mentioned keyboard and the memory 20 memorizes the above described character information or the like.

The above mentioned hard disc I/F 18 reads a program practiced by the above mentioned CPU 11 and image data of a menu picture or the like out of the above mentioned hard disc 19 and outputs them to the above mentioned memory 20 which memorizes the above described program and image data or the like.

The above mentioned CPU 11 operates so as to be displayed as synthesized or singly such image data as observed image data from the above mentioned photomagnetic disc drive, a cursor by the mouse 15, character information by the keyboard 17 and a menu picture from the hard disc 19 memorized as described above in the above mentioned memory 20 by a program memorized in the above mentioned memory 20 as described above.

The image data which are digital signals memorized in the above mentioned image memory 21 as described above are converted to analogue R,G,B video signals by the reverse quantization of the above mentioned D/A converter 22 and are output to the above mentioned high resolution monitor 23.

The above mentioned high resolution monitor 23 is to display the analogue R,G,B video signals input as described above.

The observed image data recorded in the above mentioned photomagnetic disc 10a are formed of a predetermined number of bits so that, when the above described observed image is divided, for example, by 640 dots horizontally and 480 dots vertically, the respective R,G,B color signal levels may be quantized to be, for example, of 8 bits in response to the respective dots.

The image data of the images displayed in the above mentioned high resolution monitor 23 are formed of a predetermined number of bits so that, when divided, for example, by 1024 dots horizontally and 1280 dots vertically, the respective R,G,B color signal levels may be quantized to be, for example, of 8 bits.

The operation of the thus formed medical image displaying apparatus shall be explained.

An observed image, for example, by an ultrasonic endoscope converted to a video signal by the ultrasonic diagnosing apparatus 514 is displayed as an observed image in the observation monitor 2. In case the operator of the above mentioned ultrasonic diagnosing apparatus judges it necessary to record the above described observed image, the above described observed image will be output as a black and white video signal to the above mentioned A/D converter 3, will be converted to a digital video signal, will be output as observed image data to the memory 5 and will be memorized in this memory 5.

Also, the above mentioned controller 4 applies such various data processes as a contracting process to the observed image data memorized in the above mentioned memory 5 and once memorizes the observed data in the above mentioned memory 5 or output them to the SCSI controller 6. In case the observed image data to which various data processes have been applied as described above are once memorized in the memory 5, the above mentioned controller 4 will output the above mentioned observed image data from the above mentioned memory 5 to the above mentioned SCSI controller 6 by a predetermined timing.

The control of the memory 5 and SCSI controller 6 by the above described controller 4 is made by a signal through the above mentioned bus line 4a.

The observed image and distinguishing data which are black and white images are recorded in the photomagnetic disc 10a through the photomagnetic disc drive 7 from the above mentioned SCSI controller 6.

As shown in FIG. 14, the above mentioned photomagnetic disc 10a is inserted into any one of the photomagnetic disc drives 13A, B and C. A photomagnetic disc 10b having made another examination by an electronic endoscope or the like is inserted into the remaining photomagnetic disc drives 13A, B and C.

The CPU 11 controls through the bus line 11a the SCSI controller 12, mouse I/F 14, keyboard I/F 16, hard disc I/F 18, memory 20 and image memory 21.

In the above mentioned CPU 11, by the above described control, the above mentioned hard disc I/F 18 reads out of the hard disc 19 the programs corresponding to the various processes practiced by the CPU 11.

By the above described program, there is practiced the reproducing process of displaying in the high resolution monitor 23 the image data recorded in the above mentioned photomagnetic disc 10a.

Here, the ultrasonic diagnosing apparatus 514 shall be explained.

Figure 15:
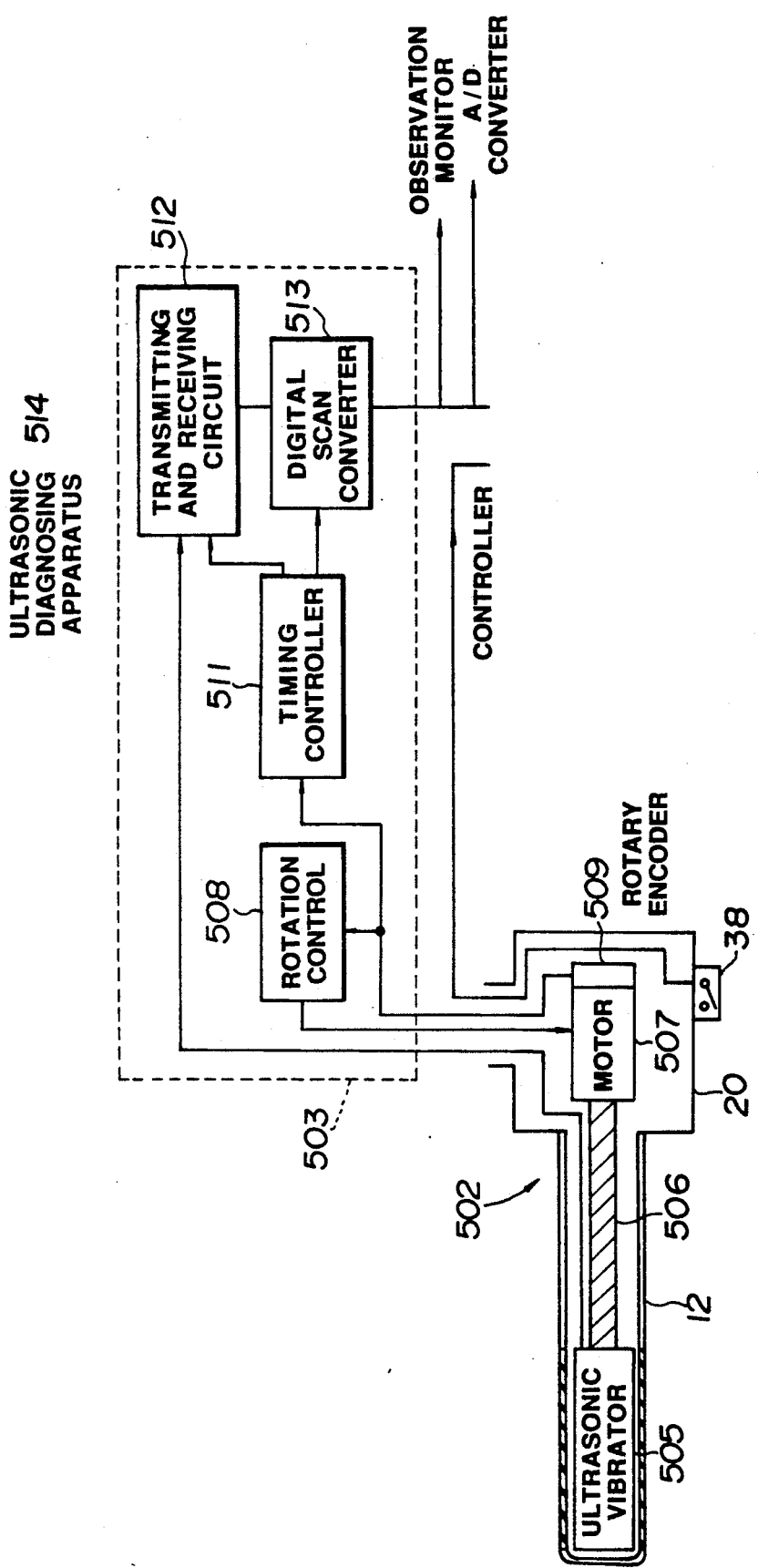

As shown in FIG. 15, in the above mentioned ultrasonic scope 502, an ultrasonic vibrator 505 is contained in the tip of an elongate insertable part 12 and is fitted to the end of a flexible shaft 506 inserted through the insertable part. This flexible shaft 506 is fitted at the other end to a rotary shaft of a motor 507 within an operating part 20 so that, when this motor 507 is rotated, the ultrasonic vibrator 505 may be rotated and driven through the flexible shaft 506.

The above mentioned motor 507 is rotated and driven by an output signal of a rotation controlling circuit 508, is fitted with such rotation number detecting means as a rotary encoder 509 and is controlled in the rotation phase by the rotation controlling 508 so that the output of of this rotary encoder 509 may coincide with a reference signal.

The output signal of the above mentioned rotary encoder 509 is input into a timing controlling circuit 511 to produce various timing signals synchronized with the rotation of the motor 507.

The above mentioned ultrasonic vibrator 505 is connected with a transmitting and receiving circuit 512 and outputs a transmitting pulse to the ultrasonic vibrator 505 as synchronized with a timing signal from the timing controlling circuit 511. By this transmitting pulse, the ultrasonic vibrator 505 ultrasonically vibrates and emits ultrasonic waves in the form of a pulse. This emitted ultrasonic wave pulse is reflected by the discontinuous part cf the acoustic impedance of the examined part and is received as an ultrasonic echo signal by the ultrasonic vibrator 505.

This ultrasonic echo signal is converted to an electric signal again, is amplified by the transmitting and receiving circuit 512, is input into a digital scan converter 513, is made a standard video signal and is output. An ultrasonic cross-sectioned image showing, for example, an examined part as cross-sectioned is displayed in the observation monitor 2.

By the way, it is obvious that the ultrasonic scope 502 may be an ultrasonic endoscope provided with an endoscope function.

The reproducing process shall be explained in the following by using FIGS. 16 and 17.

Figure 16:
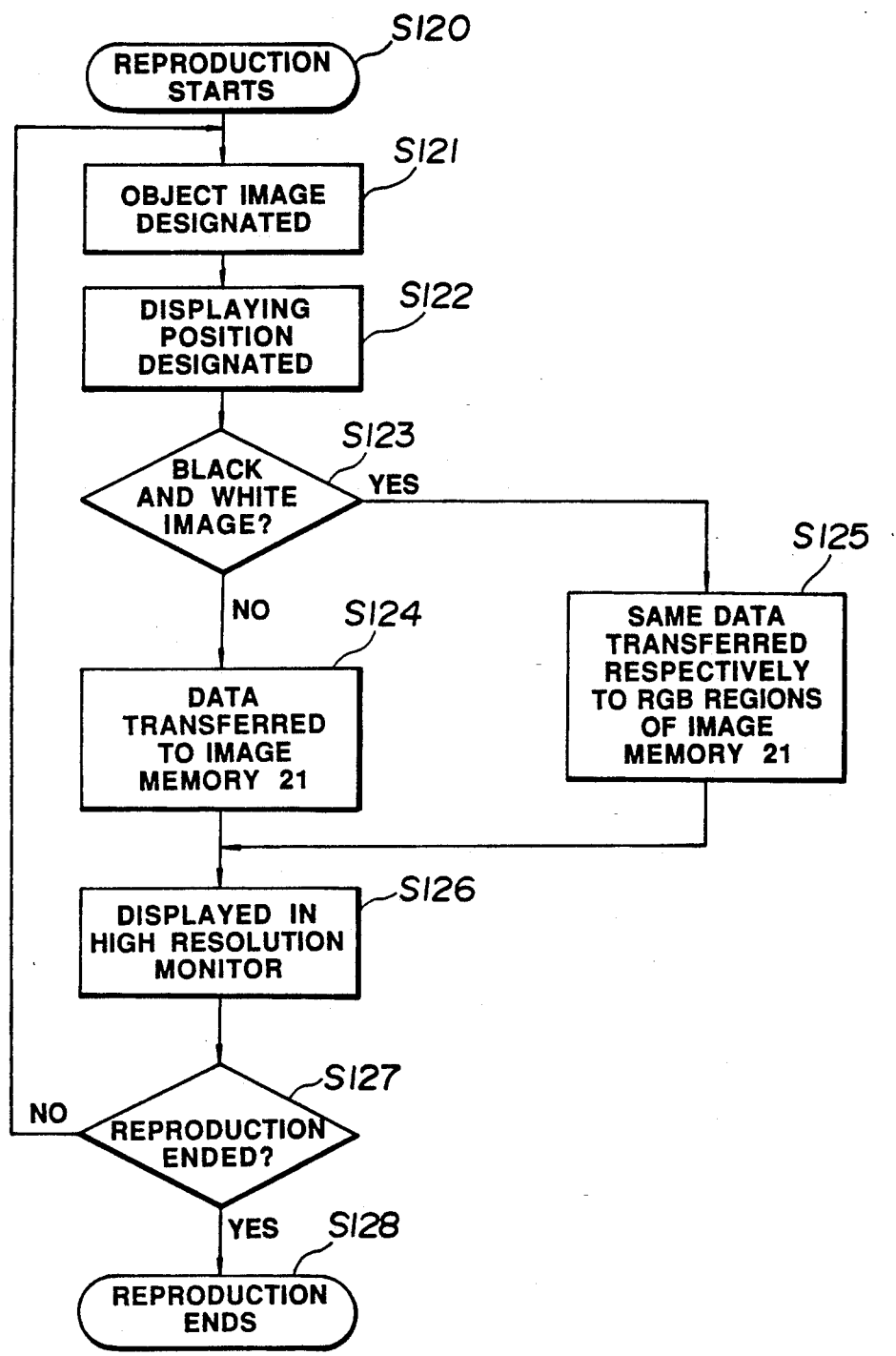

From S120 shown in FIG. 16, the reproducing process is started. In S121, an image to be an object is selected.

Figure 17:
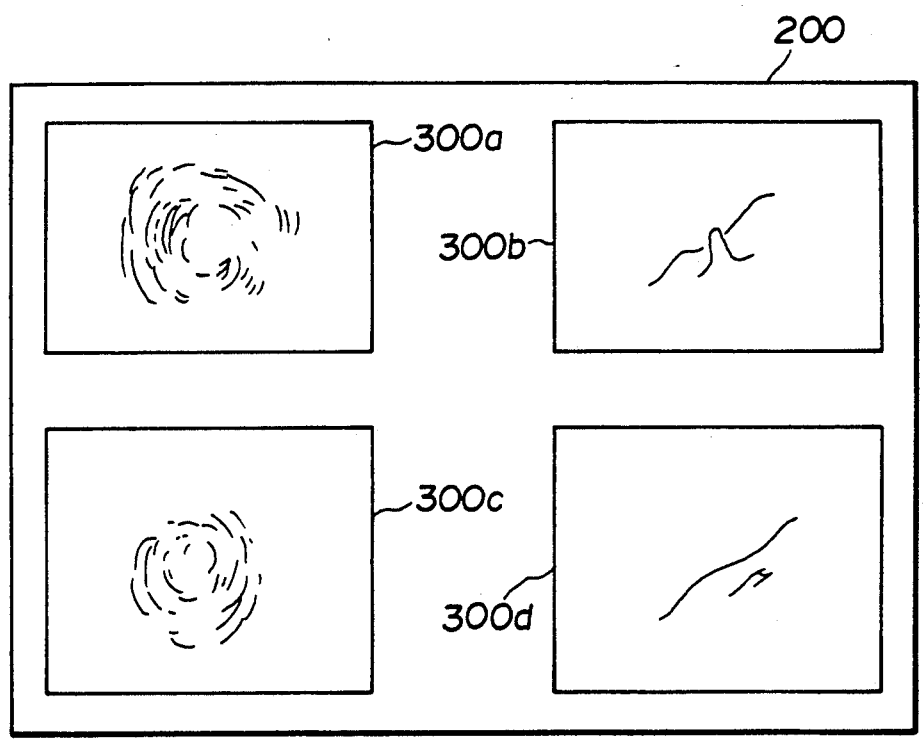

In S122, in what position of 300a, b, c and d, for example, in FIG. 17 the selected image is to be displayed is designated.

In S123, it is distinguished whether the image selected in S121 is such black and white image as an ultrasonic image.

In S123, when it is distinguished to be no black and white image, in S124, the image data will be transferred to the image memory 21 and, in S126, will be displayed in the high resolution monitor 23.

In S123, when it is distinguished to be a black and white image, in S125, the black and white data will be transferred the same to the respective R,G,B color regions of the image memory 121 and, in S126, will be displayed. In S127, if the reproduction ends, the process will end.

In S127, if the process is continued, in S121 the image will be selected again and the above operation will be repeated.

Thus, according to the second embodiment, with one TV monitor, images by a plurality of examinations and examinations different in the method, for example, video scope color images and ultrasonic scope black and white images can be arranged, compared and diagnosed and therefore the diagnosing efficiency is high.

The medical image displaying apparatus of the third embodiment explained with reference to FIGS. 18 to 23 is largely divided into an observing system and diagnosing system.

Figure 18:
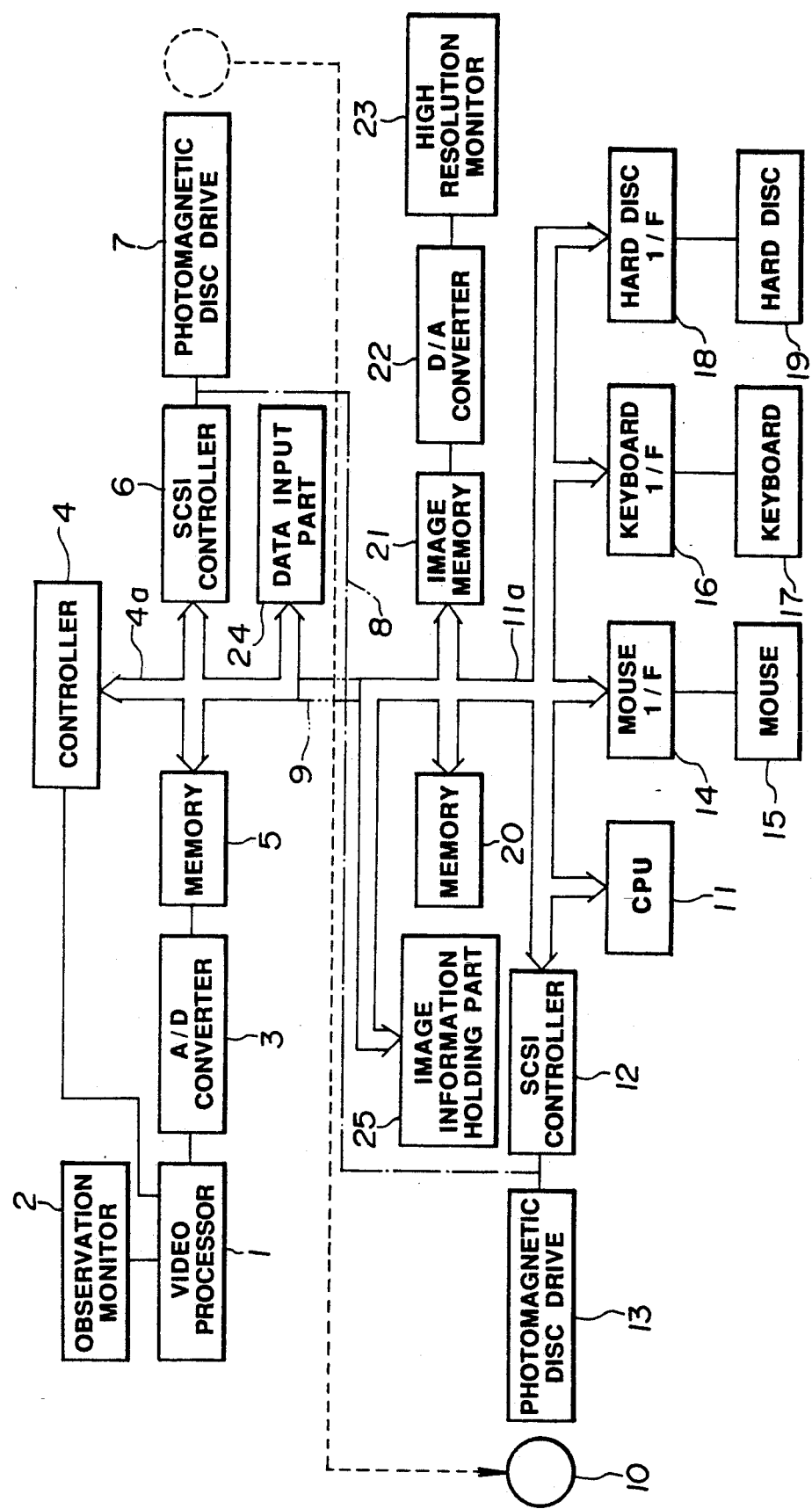

As shown in FIG. 18, the above mentioned observing system comprises a video processor 1 connected with an electronic endoscope not illustrated, obtaining an imaging signal from this electronic endoscope and converting it to a video signal, an observation monitor 2 displaying the video signal from this video processor 1, an A/D converter 3 converting the analogue R, G, B video signals of the above mentioned video processor to observed image data which are digital signals, a controller 4 controlling the later described memory 5 and SCSI controller 6, a data input part 24 inputting information or the like to be recorded, a memory 5 memorizing by the control of the above mentioned controller 4 the above described observed image data by the above mentioned A/L converter 3, the SCSI (small computer system interface) controller 6 delivering by the control of the above mentioned controller 4 the observed image data memorized in the above mentioned memory 5 to the later described photomagnetic disc drive 7 and the photomagnetic disc drive 7 recording the observed image data of the above mentioned memory 5 input from this SCSI controller 6 into, for example, a photomagnetic disc 10 which is a large capacity recording medium.

The above mentioned video processor 1 is connected at the video signal output end to the above mentioned observation monitor 2 and at the R,G,B video signal output ends to the above mentioned A/D converter 3 at the input end.

Also, the above mentioned video processor 1 is connected with the controller 4 by such standard as, for example, RS-232C.

The above mentioned A/D converter 3 is connected at the output end to the above mentioned memory 5 at the data signal end.

The above mentioned controller 4 is connected at the control signal end and data signal end through a bus line 4a to the above mentioned memory 5, SCSI controller 6 and data input part 24 at the control signal end and data signal end.

The above mentioned SCSI controller 6 is connected at the SCSI line end to the above mentioned photomagnetic disc drive 7. This SCSI line can control a plurality of microprocessor peripheral apparatus and transmit and receive data by using parallel lines (parallel core line group).

For example, a photomagnetic disc 10 which is a large capacity recording medium is to be inserted into the above mentioned photomagnetic disc drive 7.

The observed image, for example, by an electronic endoscope converted to a video signal by the above mentioned video processor 1 is to be displayed as an observed image in the above mentioned observation monitor 2. In case it is judged by the operator of the above mentioned video processor 1 to be necessary to record the above described observed image, the designation of the record and the information relating to the record will be transmitted to the above mentioned controller 4.

The above described video signal will be output as analogue R,G,B video signals to the above mentioned A/D converter 3 which will quantize the above mentioned analogue R,G,B video signals as predetermined to convert them to digital R,G,B video signals and will output them as observed image data to the above mentioned memory 5.

The above mentioned memory 5 is to memorize the observed image data input from the above mentioned A/D converter by the control of the above mentioned controller 4.

The above mentioned controller 4 applies such various data processes as a contracting process and cutting out only the observed image region to the observed image data memorized in the above mentioned memory 5 with reference to the data of the above mentioned video processor 1 and data input part 24 and once memorizes the observed image data in the above mentioned memory 5 or outputs them to the SCSI controller 6.

In case the observed image data to which various data processes have been applied as described above are once memorized in the memory 5, the above mentioned controller 4 will output the above mentioned observed image data from the above mentioned memory 5 to the above mentioned SCSI controller 6 by a predetermined timing.

The control of the memory 5 and SCSI controller 6 by the above described controller 4 is made by a signal through the above mentioned bus line 4a.

The above mentioned SCSI controller 6 outputs to the above mentioned photomagnetic disc drive 7 the observed image data from the above mentioned memory 5 and the recorded information data relating to the records of the observed image data input as described above and the above mentioned photomagnetic disc drive 7 records the observed image data, for example, in the photomagnetic disc 10.

The above mentioned diagnosing system comprises a microprocessor (called a CPU hereinafter) 11 controlling this diagnosing system, a photomagnetic disc drive 13 reproducing observed image data from the above mentioned photomagnetic disc drive 10 and recording various informations together with these observed image data, an SCSI controller 12 controlling this photomagnetic disc drive 13, a mouse 15 giving an instruction to move a cursor coordinate on a monitor picture to any position, a mouse interface (called a mouse I/F hereinafter) 14 coordinating the signal of this mouse 15 and the signal of the above mentioned CPU 11, a keyboard 17 inputting various informations to be recorded, for example, into the above mentioned photomagnetic disc 10, a keyboard interface (called a keyboard I/F hereinafter) 16 coordinating the signal of this keyboard 17 and the signal of the above mentioned CPU 11, a hard disc 19 in which are recorded such various data as a practice program and image data of a menu picture, a hard disc interface (called a hard disc I/F hereinafter) 18 coordinating the signal of this hard disc 19 and the signal of the above mentioned CPU 11, a memory 20 used as various process operating regions of the above mentioned CPU 11, an image information holding part 25 controlling the display of the image, an image memory 21 memorizing displaying digital R,G,B video signals, a D/A converter 22 reversely quantizing image data which are digital signals of the above mentioned image memory 21 and converting them to analogue R,G,B video signals and a high resolution monitor 23 displaying the analogue R,G,B video signals converted by this D/A converter 22.

The control signal end and data signal end of the above mentioned CPU 11 are connected through a bus line 11a to the control signal ends and data signal ends of the above mentioned S(SI controller 12, mouse I/F 14, keyboard I/F 16, hard disc I/F 18, memory 20, image information holding part 25 and image memory 21.

The SCSI line of the above mentioned controller 12 is connected to the above mentioned photomagnetic disc drive.

The above mentioned image memory 21 is connected at the data signal end to the above mentioned D/A converter 22 at the input end and this D/A converter 22 is connected at the output end to the above mentioned high resolution monitor 23.

Such large capacity memorizing medium as, for example, the photomagnetic disc 10 is to be inserted into the above mentioned photomagnetic disc drive 7.

The above mentioned CPU 11 is to control through the above mentioned bus line 11a the above mentioned SCSI controller 12, mouse I/F 14, keyboard I/F 16, hard disc I/F 18, memory 20, image information holding part 25 and image memory 21.

The above mentioned SCSI controller 12 controls the above mentioned photomagnetic disc drive 10, reads out the above described observed image data and recorded information data recorded in the above described system and outputs them to the above mentioned memory 20.

The above mentioned memory 20 is to memorize the above described observed image data and recorded information data.

The above mentioned mouse I/F 14 detects a signal corresponding to the physical relative displacement of the above mentioned mouse 15 and outputs the signal to the above mentioned memory 20 which memorizes the above described displacement.

The above mentioned keyboard I/F 16 outputs to the above mentioned memory 20 a signal of character information or the like input from the above mentioned keyboard and the memory 20 memorizes the above described character information or the like.

The above mentioned hard disc I/F 18 reads a program practiced by the above mentioned CPU 11 and image data of a menu picture or the like out of the above mentioned hard disc 19 and outputs them to the above mentioned memory 20 which memorizes the above described program and image data or the like.

Also, the above mentioned hard disc I/F 18 reads out of the above mentioned hard disc 19 the image reproducing information reproducing the above described observed image data on the basis of the above described recorded information data and outputs it to the above mentioned image information holding part 25 which memorizes the above described image reproducing information.

The above mentioned CPU 11 prepares reproduced observed image data with reference to the above mentioned image information holding part 25 on the basis of the observed image data and recorded information data from the above mentioned photomagnetic disc drive memorized in the above mentioned memory as described above by the program memorized in the above mentioned memory 20 as described above.

Also, the above mentioned CPU 11 operates so as to be displayed as synthesized or singly such image data as the above described reproduced observed image data, cursor by the mouse 15 character information by the keyboard 17 and menu picture from the hard disc 19 and memorizes them as image data in the above mentioned image memory 21.

The image data which are digital signals memorized in the above mentioned image memory 21 as described above are converted to analogue R,G,B video signals by the reverse quantization of the above mentioned D/A converter 22 and are output to the above mentioned high resolution monitor 23.

The above mentioned high resolution monitor 23 is to display the analogue R,G,B video signals input as described above.

The recorded information data recorded in the above mentioned photomagnetic disc 10 are formed of such information relating to the record as, for example, the kind of the above mentioned video processor 1 or observed image data recorded by 300 dots horizontally and 300 dots vertically and such inspection data relating to the patient as, for example, the ID, patient name and inspection date.

The observed image data recorded in the above mentioned photomagnetic disc 10 are formed of a predetermined number of bits so that, when the above described observed color image is divided, for example, by 300 dots horizontally and 300 dots vertically, for example, according to the recording method of the above described recorded information data, the respective R,G,B color signal levels may be quantized to be, for example, 8 bits in response to the respective dots.

The image data of the image displayed in the above mentioned high resolution monitor 23 are formed of a predetermined number of bits so that, when divided, for example, by 1024 dots horizontally and 1280 dots vertically, the respective R,G,B color signal levels may be quantized to be, for example, 8 bits.

The operation of the thus formed medical image displaying apparatus shall be explained.

In case the operator of the video processor 1 judges it necessary to record the observed image, a control signal from the above mentioned video processor 1 will be received by the above mentioned controller 4 and the above described observed image will be memorized by the controller 4.

Also, the above mentioned controller 4 applies such various data processes as the contracting process to the observed image data memorized in the above mentioned memory 5 and once memorizes them in the above mentioned memory 5 or outputs them to the SCSI controller 6.

Also, the above mentioned controller 4 has such control table relating to the record as is shown, for example, in FIG. 9, applies a data process of cutting out only the observed image region with reference to the above mentioned control table to the observed image data memorized in the above mentioned memory 5 on the basis of the information from the above mentioned video processor 1 or data input part 24 and once memorizes the observed image region in the above mentioned memory 5 or outputs it to the SCSI controller 6.

Also, the above mentioned controller 4 once memorizes in the above mentioned memory 5 the apparatus code of FIG. 19 used in the above described record and such recorded information data as the patient ID and inspection data input from the video processor 1 or data input part 24 or outputs them to the SCSI controller 6.

In case the observed image data and recorded information data to which various data processes have been applied as described above, the above mentioned controller 4 will output the above mentioned observed image data from the above mentioned memory 5 to the above mentioned SCSI controller 6 by a predetermined timing.

The above described observed image data and recorded information data are recorded in the photomagnetic disc 10 inserted into the above mentioned photomagnetic disc drive 7 as, for example, in FIG. 20 from the above mentioned SCSI controller 6.

The control of the memory 5 and SCSI controller 6 by the above described controller 4 is made by a signal through the above mentioned bus line 4a.

The photomagnetic disc 10 recorded by the above mentioned photomagnetic disc drive 7 is inserted into the photomagnetic disc drive 13 as shown in FIG. 18.

The above mentioned CPU 11 reads programs corresponding to various processes practiced by the above mentioned CPU 11 out of the hard disc 19 through the above mentioned hard disc I/F 18.

Also, the above mentioned CPU 11 reads the image reproducing information, for example, such control table as in FIG. 19 out of the hard disc 19 through the above mentioned hard disc I/F 18 and memorizes it in the image information holding part 25.

The reproducing process of displaying in the high resolution monitor 23 the image data recorded in the above mentioned photomagnetic disc 10 is practiced by the above described program.

Figure 23:
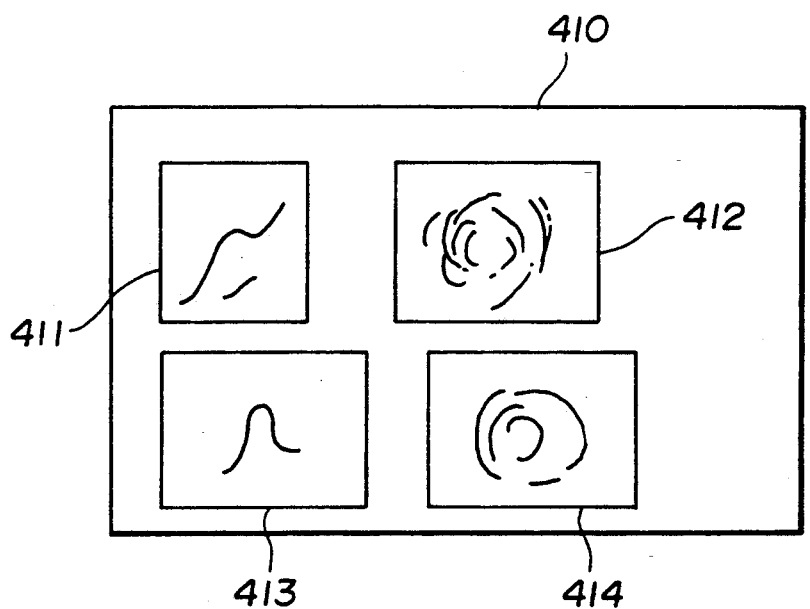
Figure 22:
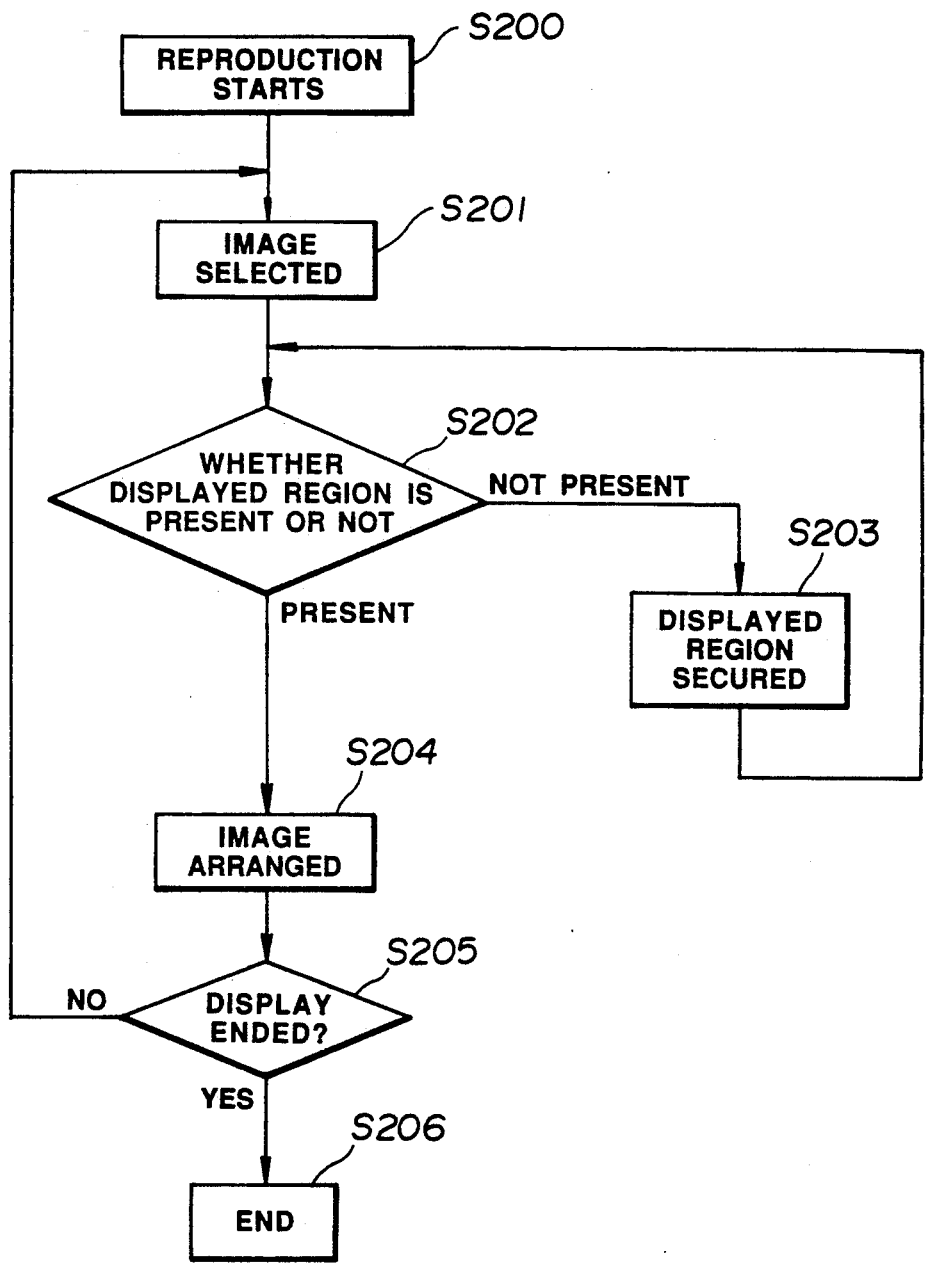

The above described reproducing process shall be explained by using FIGS. 22 and 23.

In S200, when the reproduction is started, in S201, the user will select a desired image to be inspected by the designation, for example, of the inspection data and contracted images from among the photomagnetic discs 10 inserted in the above mentioned photomagnetic disc drive 13, for example, by the keyboard 17 and mouse 15.

In the above mentioned S201, when the image is selected, in S202, the above mentioned CPU 11 will read out in the above mentioned memory 20 the observed image data and recorded information data recorded in the photomagnetic disc 10 and will apply a process, for example, of rearranging the images of the above mentioned image memory 21 with reference to the control table of the above mentioned image information holding part 25. It is judged whether the above mentioned selected image can be displayed in the undisplayed region. When it can be displayed, the process will be shifted to S204.

In the above mentioned S202, when the selected image can not be displayed, the process will be shifted to S203.

In the above mentioned S203, for example, the user designates by the keyboard 17 and mouse 15 the position of such image to be deleted to secure the displaying region of the selected image as, for example, the image 411 of the picture 410 in FIG. 23.

In the above mentioned S203, when the displaying region is secured, in S202, the process will be made again.

In the above mentioned S204, the above mentioned CPU 11 arranges and displays the observed images of the observed image data and recorded information data read out of the above mentioned memory in S202 in such position of the above mentioned image memory 21 as, for example, the position of the image 411 of the picture 410 in FIG. 23 with reference to the control table of the above mentioned image information holding part 25.

In the above mentioned S204, when the image is displayed, in S205, the reproducing process or not is selected and, when the process is to end, in S206, it will be ended.

In the above mentioned S205, when a different image is to be selected again, the process will return to S201 and the image is selected again in the same or different inspection and the above operation is repeated.

By the way, in the above mentioned S203, in order to secure the displaying region, the user may register the displaying method in advance and may input the information, for example, as to be from the first display or from the same kind of inspection and the above mentioned CPU 11 may secure the displaying region under the above described condition.

The above mentioned control table shall be explained in the following by using FIGS. 19 and 21.

There are various displaying forms for the medical diagnosing apparatus, for example, the above mentioned video processor 1.

Figure 21:
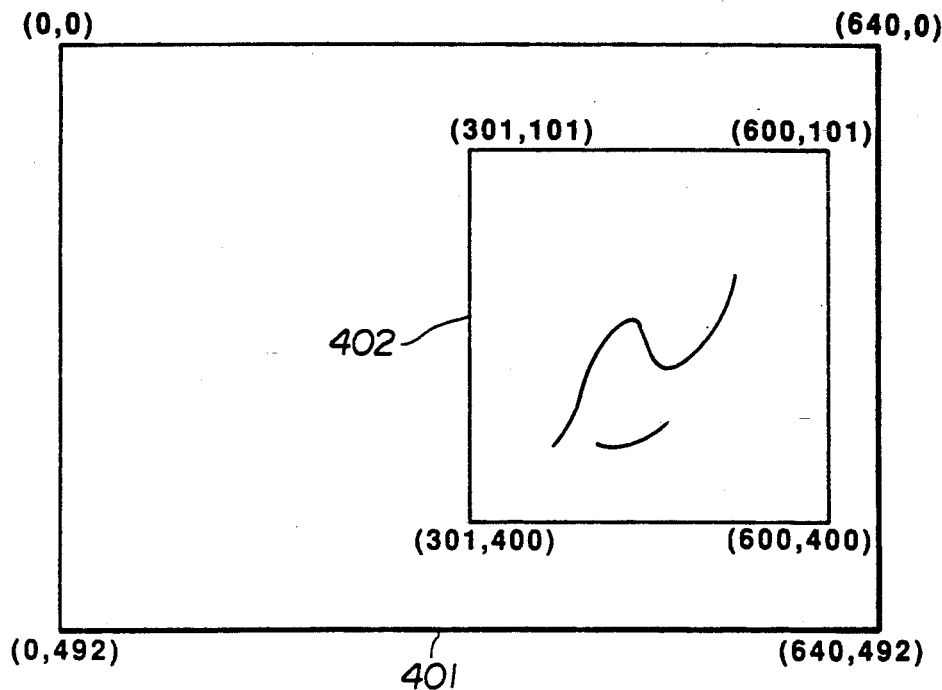

The displaying form of the video processor A, for example, in FIG. 19 is shown in FIG. 21.

In FIG. 21, the reference numeral 401 represents a displaying area and vertical and horizontal coordinates of a TV monitor, for example, of the NTSC standard.

In the above mentioned FIG. 21, the reference numeral 402 represents a displaying area and vertical and horizontal coordinates of an observed image of the above mentioned video processor A.

The displaying form shown in FIG. 21 is recorded as in FIG. 19 and a new apparatus can be also additionally registered.

By the way, in this embodiment, the recording capacity is reduced by using the control table but all the image regions may be recorded and may be arranged on the picture in FIG. 23.

That is to say, in this embodiment, a plurality of observed images are displayed in the same displaying apparatus, therefore are not influenced by the reproductivity of colors of the monitor or the like and can be compared under the same conditions at the same time and therefore there is an effect that the diagnosing function improves.

It is apparent that, in this invention, working modes differing in a wide range can be formed on the basis of this invention without deviating from the spirit and scope of the invention. This invention is not restricted by its specific working mode except being limited by the appended claims.

What is claimed is:

1. A medical image displaying method which retains the characteristics of images of first observed image data without varying the resolution of said first observed image data, comprising the steps of:
   synthesizing other image data with the first observed image data to produce second image data having a plurality of observed image data including at least the above mentioned first observed image data, and
   displaying the second image data on a displaying means capable of displaying an image having a larger amount of information than the amount of said first observed image data.

2. A medical image displaying method according to claim 1, wherein the number of bits of the first observed image data is not varied.

3. A medical image displaying apparatus for simultaneously displaying a plurality of observed images, characterized by being provided with an image synthesizing means for synthesizing other image data with first observed image data while retaining the characteristic of an image of the first observed image data without varying the resolution of said first observed image data to produce second image data provided with a plurality of observed image data including at least the above mentioned first observed image data.

4. A medical image displaying apparatus, comprising:
   a reproducing means for reproducing observed image data recorded in a recording medium;
   an image data recording means for recording various image data;
   an input means for inputting various data;
   an image synthesizing means for selecting one of the image data of said image data recording means on the basis of the data input by said input means and synthesizing the plurality of observed image data selected by said input means among the observed image data reproduced by said reproducing means together with the selected image data while retaining their characteristics to produce the second image data; and
   a high resolution monitor for displaying the images of the second image data produced by said image synthesizing means, wherein said monitor has a resolution sufficiently high to be capable of displaying a greater amount of information than the information contained in the image data.

5. A medical image displaying apparatus having an observing system and diagnosing system, characterized in that:
   said observing system comprises:
   a video processor producing a video signal of an observed image of an object to be inspected;
   a data processing means for data processing the video signal produced by said video processor; and
   a recording means for recording in a recording medium recorded data including the observed image data processed by said data processing means and
   said diagnosing system comprises:
   a reproducing means for reproducing the observed image data recorded in the recording medium;
   an image data recording means for recording various image data;
   an input means for inputting various data;
   an image synthesizing means for selecting one of the image data of the image data recording means on the basis of the data input by said input means and synthesizing the plurality of observed image data selected by said input means among the observed image data reproduced by said reproducing means together with the selected image data while retaining their characteristics to produce the second image data; and a high resolution monitor for displaying the images of the second image data produced by said image synthesizing means, wherein said monitor has a resolution sufficiently high to be capable of displaying a greater amount of information than the information contained in the image data.

6. A medical image displaying apparatus having an observing system, and diagnosing system, characterized in that:

said observing system comprises:

a video processor producing a video signal of an observed image of an object to be inspected;

a data processing means for data processing the video signal produced by said video processor; and an input means for adding such information as recorded data and inspection data to the observed image data; and a recording means for recording in a recording medium the observed image data processed by said data processing means and the added data added by said input means and said diagnosing system comprises:

a reproducing means for reproducing the observed image data recorded in the recording medium;

an image data recording means for recording various image data;

an input means for inputting various data including character data;

an image synthesizing means for selecting one of the image data of the image data recording means on the basis of the data input means and synthesizing the plurality of observed image data selected by said input means among the observed image data reproduced by said reproducing means together with the selected image data while retaining their characteristics and the character data input by said input means to produce the second image data; and a high resolution monitor for displaying the images of the second image data produced by said image synthesizing means, wherein said monitor has a resolution sufficiently high to be capable of displaying a greater amount of information than the information contained in the image data.

7. A medical image displaying apparatus having an observing system and diagnosing system, characterized in that:

said observing system comprises:

an ultrasonic diagnosing means for producing an ultrasonic video signal of an object to be inspected;

a data processing means for data processing the video signal produced by said ultrasonic diagnosing means; and a recording means for recording in a recording medium the recorded data including the observed image data processed by said data processing means and said diagnosing system comprises:

a reproducing means for reproducing the observed image data recorded in the recording medium;

an image data recording means for recording various image data;

an input means for inputting various data;

an image synthesizing means for selecting one of the image data of the image data recording means on the basis of the data input by said input means and synthesizing the plurality of observed image data selected by said input means among the observed image data reproduced by said reproducing means together with the selected image data while retaining their characteristics to produce the second image data; and a high resolution monitor for displaying the images of the second image data produced by said image synthesizing means, wherein said monitor has a resolution sufficiently high to be capable of displaying a greater amount of information than the information contained in the image data.

8. A medical image displaying apparatus according to any one of claims 5, 6 and 7, wherein said data processing means is to apply a contracting process to the observed image data.

9. A medical image displaying apparatus according to any one of claims 5, 6 and 7 characterized in that said data processing means is a process of cutting out only an observed image region for observed image data.

10. A medical image displaying apparatus according to any one of claims 5, 6 and 7 characterized in that said image data recording means is to record a plurality of menu picture data.

11. A medical image displaying apparatus according to claim 10 characterized in that said menu picture data comprise at least one of a comment image displaying a plurality of contracted observed images and various informations, a plurality of contracted observed images and a magnified observed image, a plurality of contracted observed images and a plurality of observed images.

12. A medical image displaying apparatus according to any one of claims 5, 6 and 7 characterized in that the data recorded in said recording medium include recorded data and inspection data, observed image data and contracted observed image data obtained by contracting these observed image data.

13. A medical image displaying apparatus according to any one of claims 4, 5, 6 and 7 characterized in that said reproducing means reproducing the observed image data from the recording medium has a recording function of recording various informations together with the observed image data.

14. A medical image displaying apparatus according to any one of claims 5, 6 and 7 characterized in that the observed image data recorded in the recording medium are formed of a predetermined number of bits quantized so that, when the observed image is divided by a predetermined number of dots horizontally and vertically, the respective R,G,B color signal levels may be of predetermined bits in response to the respective dots.

15. A medical image displaying apparatus according to any one of claims 4, 5, 6 and 7 characterized in that the observed image data displayed in the high resolution monitor are formed of a predetermined number of bits quantized so that, when the observed image is divided by a predetermined number of dots horizontally and vertically, the respective R,G,B color signal levels may be of predetermined bits in response to the respective dots.

* * * * *